(12) United States Patent
Rajasekhar

(10) Patent No.: US 10,463,642 B2
(45) Date of Patent: Nov. 5, 2019

(54) METHODS OF TREATING HEART FAILURE DISEASES USING PRODRUGS OF METHYL HYDROGEN FUMARATE

(71) Applicant: Vijaykumar Rajasekhar, Apple Valley, CA (US)

(72) Inventor: Vijaykumar Rajasekhar, Apple Valley, CA (US)

(*) Notice: Subject to any disclaimer, the term of this patent is extended or adjusted under 35 U.S.C. 154(b) by 100 days.

(21) Appl. No.: 15/395,977

(22) Filed: Dec. 30, 2016

(65) Prior Publication Data

US 2017/0216242 A1 Aug. 3, 2017

Related U.S. Application Data

(60) Provisional application No. 62/289,881, filed on Feb. 1, 2016.

(51) Int. Cl.
*A61K 45/06* (2006.01)
*A61K 31/225* (2006.01)

(52) U.S. Cl.
CPC ............ *A61K 31/225* (2013.01); *A61K 45/06* (2013.01)

(58) Field of Classification Search
CPC .............................. A61K 45/06; A61K 31/225
See application file for complete search history.

(56) References Cited

U.S. PATENT DOCUMENTS

| | | | |
|---|---|---|---|
| 3,580,918 A | 5/1971 | Bodnarjuk et al. | |
| 4,515,974 A | 5/1985 | Zecher et al. | |
| 4,851,439 A | 7/1989 | Speiser et al. | |
| 5,149,695 A | 9/1992 | Speiser et al. | |
| 5,424,332 A | 6/1995 | Speiser et al. | |
| 5,451,667 A | 9/1995 | Speiser et al. | |
| 5,723,558 A | 3/1998 | Oishi et al. | |
| 6,306,900 B1 | 10/2001 | Haeberlin et al. | |
| 6,355,676 B1 | 3/2002 | Joshi et al. | |
| 6,436,992 B1 | 8/2002 | Joshi et al. | |
| 6,509,376 B1 | 1/2003 | Joshi et al. | |
| 7,612,110 B2 | 11/2009 | Joshi et al. | |
| 7,619,001 B2 | 11/2009 | Joshi et al. | |
| 7,803,840 B2 | 9/2010 | Joshi et al. | |
| 7,915,310 B2 | 3/2011 | Joshi et al. | |
| 8,148,414 B2 | 4/2012 | Gangakhedkar et al. | |
| 8,399,514 B2 | 3/2013 | Lukashev et al. | |
| 8,524,773 B2 | 9/2013 | Joshi et al. | |
| 8,980,832 B2 * | 3/2015 | Joshi .................... | A61K 31/231 514/16.4 |
| 2003/0018072 A1 | 1/2003 | Joshi et al. | |
| 2004/0054001 A1 | 3/2004 | Joshi et al. | |
| 2007/0027076 A1 * | 2/2007 | Joshi .................... | A61K 31/231 514/310 |
| 2007/0248662 A1 | 10/2007 | Joshi et al. | |
| 2007/0248663 A1 | 10/2007 | Joshi et al. | |
| 2008/0004344 A1 | 1/2008 | Nilsson et al. | |
| 2008/0227847 A1 | 9/2008 | Nilsson et al. | |
| 2008/0233185 A1 | 9/2008 | Joshi et al. | |
| 2008/0299196 A1 | 12/2008 | Nilsson et al. | |
| 2008/0300217 A1 | 12/2008 | Nilsson | |
| 2009/0082260 A1 | 3/2009 | Lamb et al. | |
| 2009/0181085 A1 | 7/2009 | Joshi et al. | |
| 2009/0182047 A1 | 7/2009 | Joshi et al. | |
| 2009/0304790 A1 | 12/2009 | Nilsson et al. | |
| 2011/0124615 A1 | 5/2011 | Joshi et al. | |
| 2013/0004526 A1 | 1/2013 | Joshi et al. | |
| 2015/0265707 A1 * | 9/2015 | Manthati ................ | A61K 47/14 424/451 |

FOREIGN PATENT DOCUMENTS

| | | |
|---|---|---|
| CA | 2248955 A1 | 4/1998 |
| WO | 1998052549 A2 | 11/1998 |
| WO | 2002055066 A1 | 7/2002 |
| WO | 2002055067 A2 | 7/2002 |
| WO | 2005023241 A1 | 3/2005 |
| WO | 2006050730 A1 | 5/2006 |
| WO | 2007042034 A1 | 4/2007 |

OTHER PUBLICATIONS

Heart-Failure, 2015, https://web.archive.org/web/20151202102715/http://www.mayoclinic.org/diseases-conditions/heart-failure/basics/treatment/con-20029801.*
Heart_failure_with_preserved_ejec, 2015, https://web.archive.org/web/20160120183220/https://en.wikipedia.org/wiki/Heart_failure_with_preserved_ejection_fraction.*
Cardiac-Insufficiency, 2015, https://web.archive.org/web/20150506180705/http://www.wisegeekhealth.com/what-is-cardiac-insufficiency.htm.*
Lam et al., 2018, https://www.thecardiologyadvisor.com/cardiology/treating-heart-failure-with-preserved-ejection-fraction/article/583072/.*
Oghlakian et al., Mayo Clin. Proc., Jun. 2011, 86(6), 531-539.*
Ashrafian et al. article entitled "Fumarate is Cardioprotective via Activation of the Nrf2 Antioxidant Pathway," Cell Metab. Mar. 7, 2012;15(3):361-71.
Pearl et al. article entitled "Fumarate-Enriched Blood Cardioplegia Results in Complete Functional Recovery of Immature Myocardium," Ann. Thorac. Surg. 1993;57:1636-1641, 1994 by The Society of Thoracic Surgeons.
Tavazzi et al. article entitled "Effect of rosuvastatin in patients with chronic heart failure (the GISSI-HF trial): a randomised, double-blind, placebo-controlled trial," Lancet. Oct. 4, 2008;372(9645):1231-9.
Mudd, et al. article entitled "Tackling heart failure in the twenty-first century," Nature Publishing Group, 2008;451:919-928.
Paulus et al. article entitled "A Novel Paradigm for Heart Failure With Preserved Ejection Fraction: Comorbidities Drive Myocardial Dysfunction and Remodeling Through Coronary Microvascular Endothelial Inflammation," J Am Coll Cardiol 2013; 62: 263-271.

(Continued)

*Primary Examiner* — Sun Jae Yoo
(74) *Attorney, Agent, or Firm* — Aurora Consulting LLC; Ashley Sloat

(57) ABSTRACT

Pharmaceutical compositions comprising prodrugs of methyl hydrogen fumarate, and methods of using prodrugs of methyl hydrogen fumarate and pharmaceutical compositions thereof for treating heart failure diseases such heart failure with preserved ejection fraction (HFPEF) alone or in combination with statins (HMG-CoA reductase inhibitors) are disclosed.

10 Claims, No Drawings

(56) References Cited

OTHER PUBLICATIONS

Pitt et al. article entitled "Spironolactone for Heart Failure with Preserved Ejection Fraction," N Engl J Med. Apr. 10, 2014;370(15):1383-92.
Redfield et al. article entitled "Effect of Phosphodiesterase-5 Inhibition on Exercise Capacity and Clinical Status in Heart Failure with Preserved Ejection Fraction: A Randomized Clinical Trial," JAMA. Mar. 27, 2013;309(12):1268-77.
Zhou et al. article entitled "The Role of Nrf2-Mediated Pathway in Cardiac Remodeling and Heart Failure," Oxid Med Cell Longev. 2014;2014:260429.
Zuo et al. article eneitled "Heart failure with preserved ejection fraction: defining the function of ROS and NO," J Appl Physiol. May 14, 2015:jap.01149.2014.
From et al. articled entitled "Heart Failure with Preserved Ejection Fraction: Pathophysiology and Emerging Therapies," Cardiovasc Ther. Aug. 2011;29(4):e6-21.
Tecfidera NDA 204063—FDA Approved Labeling Text dated Mar. 27, 2013, Full Prescribing Information, Reference ID: 3283381.
Wikipedia definition "Heart failure with preserved ejection fraction," printed Oct. 19, 2017 from https://web.archive.org/web/20160120183220/https://en.wikipedia.org/wiki/Heart_failure . . . .
Mayo Clinic document entitled "Diseases and Conditions Heart Failure," printed Oct. 19, 2017 from https://web.archive.org/web/20151202102715/http://www.mayclinic.org/diseases-condit . . . .
Wisegeek article entitled "What Is Cardiac Insufficiency?" printed Oct. 19, 2017 from https://web.archive.org/web/20150506180705/http://www.wisegeekhealth.com/what-is-c . . . .
Hunt et al. Safety, Tolerability, and Pharmacokinetics of ALKS 8700, a Novel Oral Therapy for Relapsing-Remitting Multiple Sclerosis, in Healthy Subjects, P# DX37, Consortium of Multiple Sclerosis Centers, 2015 Annual Meeting May 27-30, 2015; Indianapolis, IN.
Brzyzkiewicz et al. "Incidence of chronic heart failure with preserved left ventricular ejection fraction in patients with hypertension and isolated mild diastolic dysfunction," Polskie Archiwum Medycyny Wewnętrznej 2016; vol. 126, pp. 1-2.
Lam et al. "Treating Heart Failure with Preserved Ejection Fraction," http://www.thecardiologyadvisor.com/cardiology/treating-heart-failure-with-preserved-ejection-fraction/article/583072/, printed Nov. 30, 2017.
Sharma et al. "Heart Failure With Preserved Ejection Fraction, Mechanisms, Clinical Features, and Therapies," Circulation Research [http://circres.ahajournals.org, DOI: 10.1161/CIRCRESAHA.115.302922], 2014; vol. 115, pp. 79-96.
Van Empel et al. article entitled "Inflammation in HFpEF: Key or circumstantial?" Int. J Cardiol. 2015;189:259-63. doi: 10.1016/j.ijcard.2015.04.110. Epub Apr. 15, 2015.
Asadullah et al. article entitled "Influence of monomethylfumarate on monocytic cytokine formation—explanation for adverse and therapeutic effects in psoriasis?" Arch Dermatol Res. Oct. 1997;289(11):623-30.
Gold et al. article entitled "Fumaric acid and its esters: an emerging treatment for multiple sclerosis with antioxidative mechanism of action" Clin Immunol. Jan. 2012;142(1):44-8. doi: 10.1016/j.clim.2011.02.017. Epub Feb. 26, 2011.
Haudek et al. article entitled "TNF provokes cardiomyocyte apoptosis and cardiac remodeling through activation of multiple cell death pathways" J Clin Invest. Sep. 2007;117(9):2692-701.
Plenz et al. article entitled "Activation of the cardiac interleukin-6 system in advanced heart failure" Eur J Heart Fail. Aug. 2001;3(4):415-21.

* cited by examiner

METHODS OF TREATING HEART FAILURE DISEASES USING PRODRUGS OF METHYL HYDROGEN FUMARATE

CROSS-REFERENCE TO RELATED APPLICATIONS

This application claims priority to U.S. Provisional Patent Application Ser. No. 62/289,881, filed Feb. 1, 2016, entitled "Prodrugs of Methyl Hydrogen Fumarate and their Use in Treating Heart Failure Diseases," the disclosure of which is incorporated by reference in its entirety.

INCORPORATION BY REFERENCE

All publications and patent applications mentioned in this specification are herein incorporated by reference in their entireties, as if each individual publication or patent application was specifically and individually indicated to be incorporated by reference in its entirety.

TECHNICAL FIELD

This disclosure relates to methods and compositions of treating heart failure, including heart failure with preserved ejection fraction, in a subject in need thereof by administering to the subject a therapeutically effective amount of one or more prodrugs of methyl hydrogen fumarate (MHF) alone or in combination with one or more second agents useful for treating heart failure.

BACKGROUND

Heart failure (HF) is major health problem in the United States (U.S.) and elsewhere. In the U.S., HF affects over 5 million people with approximately half a million new cases occurring each year. HF is the leading cause of hospitalizations in people over 65 years in age. HF has many potential causes and diverse clinical features. Symptoms of heart failure can include dyspnea during activity or at rest, cough, rapid weight gain, swelling in ankles, legs and abdomen, dizziness, fatigue and weakness, rapid or irregular heartbeats, nausea, palpitations, and chest pains.

About half of heart failure subjects have heart failure with preserved ejection fraction (HFPEF). Distinct from traditional HF, i.e., heart failure with reduced ejection fraction (HFREF) in which the ventricle has difficulty pumping, subjects with HFPEF show declined performance of heart ventricle, not at the time of contraction, but during the phase of diastole. HFPEF subjects show normal ejection fraction of blood pumped out of the ventricle, but the heart muscle does not quickly relax to allow efficient filling of blood returning from the body. Morbidity and mortality of HFPEF are similar to traditional HF; however, therapies that benefit traditional HF are not effective in treating or preventing HFPEF. Subjects with HFPEF have an ejection fraction of $\geq 40\%$, $\geq 45\%$, or $\geq 50\%$ depending on which definition is chosen from the literature. On the other hand, subjects with HFREF have an ejection fraction of either $\leq 35\%$ or $\leq 40\%$ depending on which definition and guidelines are used. For ease of simplicity, and not to be limiting in any way, HFPEF can be considered as having an ejection fraction $\geq 40\%$ and HFREF can be considered as having an ejection fraction $\leq 40\%$.

Other names for the two primary clinical subsets of HF are diastolic heart failure (DHF) and systolic heart failure (SHF). SHF, which is also known as heart failure with reduced ejection fraction (HFREF) involves an abnormality of the heart resulting in failure of the heart to pump blood at a rate needed for metabolizing tissues at rest and/or during exertion. DHF, also known as heart failure with preserved ejection fraction (HFPEF), is a clinical syndrome with symptoms and signs of HF, a preserved ejection fraction and abnormal diastolic function. The clinical manifestations of HFREF and HFPEF have distinct differences in risk factors, subject characteristics, and pathophysiology. Moreover, medications proven effective in HFREF have not been found to be effective in HFPEF. At present, there are no approved treatments for HFPEF.

In HFREF, medications such as beta-blockers, ace-inhibitors, angiotensin receptor blockers, isosorbide dinitrate, hydralazine, aldosterone inhibitors, and angiotensin receptor neprilysin inhibitors have been shown to provide benefit. However, these medications have not shown to be beneficial in subjects with HFPEF, and are not approved therapies for HFPEF.

Given that there are currently no approved treatments to improve survival in HFPEF, there remains, therefore, a real need in the treatment of HFPEF for a product that can improve morbidity and mortality of subjects with HFPEF.

The present disclosure addresses these needs in subjects with HFPEF, as well as in subjects at risk of developing HFPEF, due to conditions including but not limited to hypertension, diabetes, COPD, atrial fibrillation, obesity, or ischemic heart disease.

Fumaric acid esters (FAEs) are approved in Germany for the treatment of psoriasis, are being evaluated in the United States for the treatment of psoriasis and multiple sclerosis, and have been proposed for use in treating a number of immunological, autoimmune, and inflammatory diseases and conditions.

FAEs and other fumaric acid derivatives have been proposed for use in treating a wide-variety of diseases and conditions involving immunological, autoimmune, and/or inflammatory processes including psoriasis (Joshi and Strebel, WO 1999/49858; U.S. Pat. No. 6,277,882; Mrowietz and Asadullah, Trends Mol Med 2005, 111(1), 43-48; and Yazdi and Mrowietz, Clinics Dermatology 2008, 26, 522-526); asthma and chronic obstructive pulmonary diseases (Joshi et al., WO 2005/023241 and US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. Nos. 6,509,376, 6,858,750, and 7,157,423); transplantation (Joshi and Strebel, WO 2002/055063, US 2006/0205659, U.S. Pat. Nos. 6,359,003, 6,509,376, and 7,157,423; and Lehmann et al., Arch Dermatol Res 2002, 294, 399-404); autoimmune diseases (Joshi and Strebel, WO 2002/055063, U.S. Pat. Nos. 6,509,376, 7,157,423, and 2006/0205659) including multiple sclerosis (MS) (Joshi and Strebel, WO 1998/52549 and U.S. Pat. No. 6,436,992; Went and Lieberburg, US 2008/0089896; Schimrigk et al., Eur J Neurology 2006, 13, 604-610; and Schilling et al., Clin Experimental Immunology 2006, 145, 101-107); ischemia and reperfusion injury (Joshi et al., US 2007/0027076); AGE-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

FUMADERM®, an enteric coated tablet containing a salt mixture of monoethyl fumarate and dimethyl fumarate (DMF) which is rapidly hydrolyzed to monomethyl fumarate, regarded as the main bioactive metabolite, was approved in Germany in 1994 for the treatment of psoriasis. FUMADERM® is dosed three times a day (TID) with 1-2 grams/day administered for the treatment of psoriasis. FUMADERM® exhibits a high degree of intersubject variability with respect to drug absorption and food strongly reduces bioavailability. Absorption is thought to occur in the small intestine with peak levels achieved 5-6 hours after oral administration. Significant side effects occur in 70-90% of subjects (Brewer and Rogers, Clin Expt'l Dermatology 2007, 32, 246-49; and Hoefnagel et al., Br J Dermatology 2003, 149, 363-369). Side effects of current FAE therapy include gastrointestinal upset including nausea, vomiting, diarrhea and/or transient flushing of the skin.

Dimethyl fumarate (DMF) is the active component of BG-12, also known as Tecfidera®, studied for the treatment of relapsing-remitting MS (RRMS). In a Phase IIb RRMS study, BG-12 significantly reduced gadolinium-enhancing brain lesions. In preclinical studies, DMF administration has been shown to inhibit central nervous system (CNS) inflammation in murine and rat EAE. It has also been found that DMF can inhibit astrogliosis and microglial activations associated with EAE. See, e.g., US Published Application No. 2012/0165404.

Despite its benefits, dimethyl fumarate is also associated with significant drawbacks. For example, dimethyl fumarate is known to cause side effects upon oral administration, such as flushing and gastrointestinal events including, nausea, diarrhea, and/or upper abdominal pain in subjects. See, e.g., Gold et al., N. Eng. J. Med., 2012, 367(12), 1098-1107. Dimethyl fumarate is dosed two times a day (BID) or TID with a total daily dose of about 480 mg to about 1 gram or more.

Further, in the use of a drug for long-term therapy it is desirable that the drug be formulated so that it is suitable for once- or twice-daily administration to aid subject compliance. A dosing frequency of once-daily or less is even more desirable.

Another problem with long-term therapy is the requirement of determining an optimum dose, which can be tolerated by the subject. If such a dose is not determined this can lead to a diminution in the effectiveness of the drug being administered.

Accordingly, it is an object of the present disclosure to provide compositions, which are suitable for long-term administration for subjects in need of therapy of heart failure disease, including heart failure with preserved ejection fraction.

It is a further object of the present disclosure to provide the use of a pharmaceutical active agent in a manner, which enables one to achieve a tolerable steady state level for the drug in a subject being treated therewith.

Because of the disadvantages of dimethyl fumarate described above, there continues to be a need to decrease the dosing frequency, reduce side-effects and/or improve the physicochemical properties associated with DMF. There remains, therefore, a real need in the treatment of certain conditions for a product that retains the pharmacological advantages of DMF but overcomes its flaws in formulation and/or adverse effects upon administration. The present disclosure addresses these needs in subjects with heart failure disease.

SUMMARY

The present disclosure relates to methods and compositions useful in the treatment of heart failure diseases. The methods and compositions described herein comprise one or more prodrugs of methyl hydrogen fumarate (MHF) for the treatment of a heart failure disease.

In a first aspect, the heart failure disease is one of: heart failure with preserved ejection fraction (HFPEF); heart failure with ejection fraction ≥40%; diastolic heart failure; heart failure with elevated levels of TNF-α, IL-6, CRP, or TGF-β; hypertension with risk of developing HFPEF; atrial fibrillation with risk of developing HFPEF; diabetes with risk of developing HFPEF; COPD with risk of developing HFPEF; ischemic heart disease with risk of developing HFPEF; obesity with risk of developing HFPEF; chronic heart failure; compensated heart failure; and decompensated heart failure. In some embodiments, heart failure disease is heart failure with preserved ejection fraction.

In a second aspect, prodrug of methyl hydrogen fumarate (MTIF) is a compound of Formula (I):

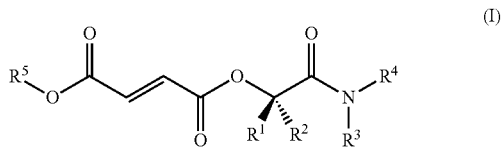

or a pharmaceutically acceptable salt thereof,
wherein:
$R^1$ and $R^2$ are independently chosen from hydrogen, $C_{1-6}$ alkyl, and substituted $C_{1-6}$ alkyl;
$R^3$ and $R^4$ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and
$R^5$ is chosen from methyl, ethyl, and $C_{3-6}$ alkyl;
wherein each substituent group is independently chosen from halogen, —OH, —CN, —CF$_3$, =O, —NO$_2$, benzyl, —C(O)NR$^{11}_2$, —R$^{11}$, —OR$^{11}$, —C(O)R$^{11}$, COOR$^{11}$, and —NR$^{11}_2$ wherein each R$^{11}$ is independently chosen from hydrogen and $C_{1-4}$ alkyl;
with the provison that when $R^5$ is ethyl; then $R^3$ and $R^4$ are independently chosen from hydrogen, $C_{1-6}$ alkyl, and substituted $C_{1-6}$ alkyl.

In one embodiment of the present disclosure, the compound is (N,N-diethylcarbamoyl)methyl methyl (2E)but-2-ene-1,4-dioate or a pharmaceutically acceptable salt thereof.

The present disclosure also provides pharmaceutical compositions comprising one or more compounds of any of the formulae described in U.S. Pat. No. 8,148,414, the disclosure of which is herein incorporated by reference in its entirety, and one or more pharmaceutically acceptable carriers for the treatment of heart failure disease. In some embodiments, the heart failure disease is heart failure with preserved ejection fraction (HFPEF).

In another embodiment a pharmaceutical composition is administered to the subject, wherein said pharmaceutical composition comprises about 200 mg to about 1200 mg of (N,N-diethylcarbamoyl)methyl methyl (2E)but-2-ene-1,4-dioate or a pharmaceutically acceptable salt thereof.

The present disclosure also provides compositions that enable improved oral, controlled- or sustained-release formulations for use in the treatment of heart failure disease.

The compositions may enable formulations with a modified duration of therapeutic efficacy for reducing heart failure disease in subjects. For example, the compositions provide therapeutically effective amounts of monomethyl fumarate in subjects for at least about 8 hours, at least about 12 hours, at least about 16 hours, at least about 20 hours or at least about 24 hours.

In some embodiments, compositions comprise a therapeutically effective amount of (N,N-diethylcarbamoyl)methyl methyl (2E)but-2-ene-1,4-dioate or a pharmaceutically acceptable salt thereof that is shown to provide MMF plasma exposure comparable to dimethyl fumarate (DMF) 120 mg to 720 mg per day.

The present disclosure also provides methods of treating a heart failure disease by administering to a subject in need thereof, a therapeutically effective amount of a compound of any of the formulae described herein, or a pharmaceutically acceptable salt, polymorph, hydrate, solvate or co-crystal thereof, such that the disease is treated.

The present disclosure also provides methods of treating heart failure with preserved ejection fraction (HFPEF) by administering to a subject in need thereof, a therapeutically effective amount of a compound of any of the formulae described herein, or a pharmaceutically acceptable salt, polymorph, hydrate, solvate or co-crystal thereof, such that the disease is treated.

The present disclosure also provides methods of reducing progression to heart failure in subjects with hypertension by administering to a subject in need thereof, a therapeutically effective amount of a compound of any of the formulae described herein, or a pharmaceutically acceptable salt, polymorph, hydrate, solvate, or co-crystal thereof.

In one embodiment, (N,N-diethylcarbamoyl)methyl methyl (2E)but-2-ene-1,4-dioate or a pharmaceutically acceptable salt thereof is administered in combination with one or more second agents useful for treating heart failure. In various embodiment, the second agent is selected from the group consisting of: a diuretic, an ace-inhibitor, a beta-blocker, an angiotensin receptor blocker, isosorbide dinitrate, hydralazine, an angiotensin receptor-neprilysin inhibitor, an aldosterone antagonist, a PDE5 inhibitor, a statin, a neprilysin inhibitor, an aldosterone inhibitor, and an antitumor necrosis factor-alpha therapy. In one embodiment, the second agent is a statin.

Another aspect of the present disclosure provides for a pharmaceutical composition comprising (a) (N,N-diethylcarbamoyl)methyl methyl (2E)but-2-ene-1,4-dioate or a pharmaceutically acceptable salt thereof and (b) a statin and one or more pharmaceutically acceptable excipients.

In some embodiments, the pharmaceutical composition comprises (N,N-diethylcarbamoyl)methyl methyl (2E)but-2-ene-1,4-dioate or a pharmaceutically acceptable salt thereof at a dose range of 200 mg to 1200 mg and the statin at a dose range of 10 mg to 80 mg.

Another aspect of the disclosure provides a method of treating a heart failure disease in a subject in need thereof, the method comprising: administering to the subject a therapeutically effective amount of (a) (N,N-diethylcarbamoyl)methyl methyl (2E)but-2-ene-1,4-dioate or a pharmaceutically acceptable salt thereof and either separately or together with (b) a statin.

The present disclosure also provides compositions and methods, which may result in decreased side effects upon administration to a subject relative to dimethyl fumarate. For example, gastric irritation and flushing are known side effects of oral administration of dimethyl fumarate in some subjects. The compositions and methods of the present disclosure can be utilized in subjects that have experienced or are at risk of developing such side effects.

The present disclosure also provides for compositions which exhibit improved physical stability relative to dimethyl fumarate. Specifically, dimethyl fumarate is known in the art to undergo sublimation at ambient and elevated temperature conditions. The compounds of the disclosure possess greater physical stability than dimethyl fumarate under controlled conditions of temperature and relative humidity. Specifically, in one embodiment, the compounds of the formulae described herein exhibit decreased sublimation relative to dimethyl fumarate.

Further, dimethyl fumarate is also known to be a contact irritant. In one embodiment, the compounds of the present disclosure exhibit reduced contact irritation relative to dimethyl fumarate. For example, the compounds of the formulae described herein exhibit reduced contact irritation relative to dimethyl fumarate.

The present disclosure also provides for compositions that exhibit decreased food effect relative to dimethyl fumarate. The bioavailability of dimethyl fumarate is known in the art to be reduced when administered with food. Specifically, in one embodiment, the compounds of the formulae described herein exhibit decreased food effect relative to dimethyl fumarate.

DETAILED DESCRIPTION

The foregoing is a summary, and thus, necessarily limited in detail. The above-mentioned aspects, as well as other aspects, features, and advantages of the present technology described below in connection with various embodiments, with reference made to the accompanying drawings.

Definitions

A dash ("—") that is not between two letters or symbols is used to indicate a point of attachment for a moiety or substituent. For example, —CONH$_2$ is bonded through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments, from 1 to 6 carbon atoms ($C_{1-6}$), in certain embodiments from 1 to 4 carbon atoms ($C_{1-4}$), and in certain embodiments, from 1 to 3 carbon atoms ($C_{1-3}$).

"Aryl" refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{6-10}$), and in certain embodiments from 6 to 8 carbon atoms ($C_{6-8}$). Aryl, however, does not encompass or overlap in any way with heteroaryl, separately defined herein.

"Arylalkyl" refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$, in certain embodiments, an arylalkyl group is $C_{6-18}$ arylalkyl, e.g., the alkanyl, alkenyl or alkynyl moiety of the arylalkyl group is $C_{1-8}$ and the aryl moiety is $C_{6-10}$. In certain embodiments, an arylalkyl group is $C_{7-12}$ arylalkyl.

"Compounds" of Formulae (I)-(IV) disclosed herein include any specific compounds within these formulae. Compounds may be identified either by their chemical structure and/or chemical name. Compounds are named using Chemistry 4-D Draw Pro, version 7.01c (ChemInnovation Software, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds of Formulae (I)-(IV) include, but are not limited to, optical isomers of compounds of Formulae (I)-(IV), racemates thereof, and other mixtures thereof. In such embodiments, a single enantiomer or diastereomer, i.e., optically active form can be obtained by asymmetric synthesis or by resolution of the racemates. Resolution of the racemates may be accomplished, for example, by conventional methods such as crystallization in the presence of a resolving agent, or chromatography using, for example, chiral stationary phases. Not withstanding the foregoing, in compounds of Formulae (I)-(IV) the configuration of the illustrated double bond is only in the E configuration (i.e. trans configuration).

Compounds of Formulae (I)-(IV) may also exist in several tautomeric forms including the enol form, the keto form, and mixtures thereof. Accordingly, the chemical structures depicted herein encompass all possible tautomeric forms of the illustrated compounds. Compounds of Formulae (I)-(IV) also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds as referred to herein may be free acid, hydrated, solvated, or N-oxides. Certain compounds may exist in multiple crystalline, co-crystalline, or amorphous forms. Compounds of Formulae (I)-(IV) include pharmaceutically acceptable salts thereof, or pharmaceutically acceptable solvates of the free acid form of any of the foregoing, as well as crystalline forms of any of the foregoing.

Compounds of Formulae (I)-(IV) also include solvates. A solvate refers to a molecular complex of a compound with one or more solvent molecules in a stoichiometric or non-stoichiometric amount. Such solvent molecules are those commonly used in the pharmaceutical art, which are known to be innocuous to a subject, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

Further, when partial structures of the compounds are illustrated, an asterisk (*) indicates the point of attachment of the partial structure to the rest of the molecule.

"Cycloalkyl" refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Cycloalkylalkyl" refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{4-30}$ cycloalkylalkyl, e.g., the alkanyl, alkenyl, or alkynyl moiety of the cycloalkylalkyl group is $C_{1-10}$ and the cycloalkyl moiety is $C_{3-20}$, and in certain embodiments, a cycloalkylalkyl group is $C_{3-20}$ cycloalkylalkyl, e.g., the alkanyl, alkenyl, or alkynyl moiety of the cycloalkylalkyl group is $C_{1-8}$ and the cycloalkyl moiety is $C_{3-12}$. In certain embodiments, a cycloalkylalkyl group is $C_{4-12}$ cycloalkylalkyl.

"Disease" refers to a disease, disorder, condition, or symptom of any of the foregoing.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ."

"Halogen" refers to a fluoro, chloro, bromo, or iodo group. In certain embodiments, halogen refers to a chloro group.

"Heteroalkyl" by itself or as part of another substituent refer to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{13}$, =N—N=, —N=N—, —N=N—NR$^{13}$, —PR$^{13}$—, —P(O)$_2$—, —POR$^{13}$, —O—P(O)$_2$—, —SO—, —SO$_2$—, —Sn(R$^{13}$)$_2$—, and the like, where each R$^{13}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example $C_{1-6}$ heteroalkyl includes groups having five carbon atoms and one heteroatom, groups having four carbon atoms and two heteroatoms, etc. In certain embodiments, each R$^{13}$ is independently chosen from hydrogen and $C_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Heteroaryl" refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. In certain embodiments, when the total number of N, S, and O atoms in the heteroaryl group exceeds one, the heteroatoms are not adjacent to one another. In certain embodiments, the total number of heteroatoms in the heteroaryl group is not more than two.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, a heteroaryl group is from 4- to 20-membered heteroaryl ($C_{4-20}$), and in certain embodiments from 4- to 12-membered heteroaryl ($C_{4-10}$). In certain embodiments, heteroaryl groups are those derived from thiophene, pyrrole, benzothiophene, benzofuran, indole, pyridine, quinoline, imidazole, oxazole, or pyrazine. For example, in certain embodiments, $C_5$ heteroaryl can be furyl, thienyl, pyrrolyl, imidazolyl, pyrazolyl, isothiazolyl, isoxazolyl.

"Heterocycloalkyl" refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system no longer contains at least one aromatic ring. Examples of heteroatoms to replace the carbon atom(s) include, but are not limited to, N, P, O, S, Si, etc. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like. In certain embodiments, a heterocycloalkyl group is $C_{5-10}$ heterocycloalkyl, $C_{5-8}$ heterocycloalkyl, and in certain embodiments, $C_{5-6}$ heterocycloalkyl.

"Leaving group" has the meaning conventionally associated with it in synthetic organic chemistry, i.e., an atom or a group capable of being displaced by a nucleophile and includes halogen such as chloro, bromo, fluoro, and iodo, acyloxy (alkoxycarbonyl) such as acetoxy and benzoyloxy, aryloxycarbonyl, mesyloxy, tosyloxy, trifluoromethanesulfonyloxy, aryloxy such as 2,4-dinitrophenoxy, methoxy, N,O-dimethylhydroxylamino, p-nitrophenolate, imidazolyl, and the like.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hickel rule (4n+2). Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Subject" or a "subject in need thereof" as used herein is a mammal having a heart failure disease. In one embodiment, a subject in need thereof has heart failure with preserved ejection fraction (HFPEF) or is at risk of developing HFPEF. The mammal can be e.g., any mammal, e.g., a human, primate, bird, mouse, rat, fowl, dog, cat, cow, horse, goat, camel, sheep or a pig. In one embodiment, the mammal is a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a subject and which does not destroy the pharmacological activity thereof and which is non-toxic when administered in doses sufficient to provide a therapeutically effective amount of the compound.

"Pharmaceutical composition" refers to a compound of Formulae (I)-(IV) and at least one pharmaceutically acceptable vehicle, with which the compound of Formulae (I)-(IV) is administered to a subject.

"Substituted" refers to a group in which one or more hydrogen atoms are independently replaced with the same or substituent group(s). In certain embodiments, each substituent group is independently chosen from halogen, —OH, —CN, —CF$_3$, =O, —NO$_2$, benzyl, —C(O)NH$_2$, —R$^{11}$, —OR$^{11}$, —C(O)R$^{11}$, —COOR$^{11}$, and —NR$^{11}$$_2$ wherein each R$^{11}$ is independently chosen from hydrogen and C$_{1-4}$ alkyl. In certain embodiments, each substituent group is independently chosen from halogen, —OH, —CN, —CF$_3$, —NO$_2$, benzyl, —R$^{11}$, —OR$^{11}$, and —NR$^{11}$$_2$ wherein each R$^{11}$ is independently chosen from hydrogen and C$_{1-4}$ alkyl. In certain embodiments, each substituent group is independently chosen from halogen, —OH, —CN, —CF$_3$, =O, —NO$_2$, benzyl, —C(O)NR$^{11}$$_2$, —R$^{11}$, —OR$^{11}$, C(O)R, —COOR$^{11}$, and —NR$^{11}$$_2$ wherein each R$^{11}$ is independently chosen from hydrogen and C$_{1-4}$ alkyl. In certain embodiments, each substituent group is independently chosen from —OH, C$_{1-4}$ alkyl, and —NH$_2$.

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the subject. In certain embodiments, "treating" or "treatment" refers to delaying the onset of the disease or at least one or more symptoms thereof in a subject which may be exposed to or predisposed to a disease even though that subject does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the subject to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a subject. A therapeutically effective dose may vary from compound to compound, and from subject to subject, and may depend upon factors such as the condition of the subject and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

The present disclosure provides methods of treating a heart failure disease by administering a compound of Formula (I), (II), (III) or (IV), and pharmaceutical compositions containing a compound of Formula (I), (II), (III) or (IV).

Compounds

Certain embodiments of methods disclosed herein use an compound of Formula (I):

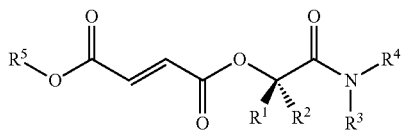

(I)

or a pharmaceutically acceptable salt thereof,
wherein:

$R^1$ and $R^2$ are independently chosen from hydrogen, $C_{1-6}$ alkyl, and substituted $C_{1-6}$alkyl;

$R^3$ and $R^4$ are independently chosen from hydrogen, $C_{1-6}$ alkyl, substituted $C_{1-6}$alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and $R^5$ is chosen from methyl, ethyl, and $C_{3-6}$ alkyl;

wherein each substituent group is independently chosen from halogen, —OH, —CN, —CF$_3$, =O, —NO$_2$, benzyl, —C(O)NR$^{11}_2$, —R$^{11}$, —OR$^{11}$, —C(O)R$^{11}$, —COOR$^{11}$, and —NR$^{11}_2$ wherein each R$^{11}$ is independently chosen from hydrogen and $C_{1-4}$ alkyl;

with the proviso that when $R^5$ is ethyl, then $R^3$ and $R^4$ are chosen from hydrogen, $C_{1-6}$ alkyl, and substituted $C_{1-6}$ alkyl.

In certain embodiments of a method using a compound of Formula (I), each substituent group is independently chosen from halogen, —OH, —CN, —CF$_3$, —R$^{11}$, —OR$^{11}$, and —NR$^{11}_2$ wherein each R$^{11}$ is independently chosen from hydrogen and $C_{1-4}$ alkyl. In certain embodiments, each substituent group is independently chosen from —OH, and —COOH.

In certain embodiments of a method using a compound of Formula (I), each substituent group is independently chosen from =O, $C_{1-4}$ alkyl, and —COOR$^{11}$ wherein R$^{11}$ is chosen from hydrogen and $C_{1-4}$ alkyl.

In certain embodiments of a method using a compound of Formula (I), each of $R^1$ and $R^2$ is hydrogen.

In certain embodiments of a method using a compound of Formula (I), one of $R^1$ and $R^2$ is hydrogen and the other of $R^1$ and $R^2$ is $C_{1-4}$ alkyl.

In certain embodiments of a method using a compound of Formula (I), one of $R^1$ and $R^2$ is hydrogen and the other of $R^1$ and $R^2$ is chosen from methyl, ethyl, n-propyl, isopropyl, n-butyl, isobutyl, sec-butyl, and tert-butyl.

In certain embodiments of a method using a compound of Formula (I), one of $R^1$ and $R^2$ is hydrogen and the other of $R^1$ and $R^2$ is methyl.

In certain embodiments of a method using a compound of Formula (I), $R^3$ and $R^4$ are independently chosen from hydrogen and $C_{1-6}$ alkyl.

In certain embodiments of a method using a compound of Formula (I), $R^3$ and $R^4$ are independently chosen from hydrogen and $C_{1-4}$ alkyl.

In certain embodiments of a method using a compound of Formula (I), $R^3$ and $R^4$ are independently chosen from hydrogen, methyl, and ethyl.

In certain embodiments of a method using a compound of Formula (I), each of $R^3$ and $R^4$ is hydrogen; in certain embodiments, each of $R^3$ and $R^4$ is methyl; and in certain embodiments, each of $R^3$ and $R^4$ is ethyl.

In certain embodiments of a method using a compound of Formula (I), $R^3$ is hydrogen; and $R^4$ is chosen from $C_{1-4}$ alkyl, substituted $C_{1-4}$ alkyl wherein the substituent group is chosen from =O, —OR$^{11}$, —COOR$^{11}$, and —NR$^{11}_2$, wherein each R$^{11}$ is independently chosen form hydrogen and $C_{1-4}$ alkyl.

In certain embodiments of a method using a compound of Formula (I), $R^3$ is hydrogen; and $R^4$ is chosen from $C_{1-4}$ alkyl, benzyl, 2-methoxyethyl, carboxymethyl, carboxypropyl, 1,2,4-thiadoxolyl, methoxy, 2-methoxycarbonyl, 2-oxo (1,3-oxazolidinyl), 2-(methylethoxy)ethyl, 2-ethoxyethyl, (tert-butyloxycarbonyl)methyl, (ethoxycarbonyl)methyl, carboxymethyl, (methylethyl)oxycarbonylmethyl, and ethoxycarbonylmethyl.

In certain embodiments of a method using a compound of Formula (I), $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a method using a compound of Formula (I), $R^3$ and $R^4$ together with the nitrogen to which they are bonded form a ring chosen from a $C_5$ heterocycloalkyl, substituted $C_5$ heterocycloalkyl, $C_5$ heteroaryl, and substituted $C_5$ heteroaryl ring. In certain embodiments of a method using a compound of Formula (I), $R^3$ and $R^4$ together with the nitrogen to which they are bonded form a ring chosen from a $C_6$ heterocycloalkyl, substituted $C_6$ heterocycloalkyl, $C_6$ heteroaryl, and substituted $C_6$ heteroaryl ring. In certain embodiments of a method using a compound of Formula (I), $R^3$ and $R^4$ together with the nitrogen to which they are bonded form a ring chosen from piperazine, 1,3-oxazolidinyl, pyrrolidine, and morpholine ring.

In certain embodiments of a method using a compound of Formula (I), $R^3$ and $R^4$ together with the nitrogen to which they are bonded form a $C_{5-10}$ heterocycloalkyl ring.

In certain embodiments of a method using a compound of Formula (I), $R^5$ is methyl.

In certain embodiments of a method using a compound of Formula (I), $R^5$ is ethyl.

In certain embodiments of a method using a compound of Formula (I), $R^5$ is $C_{3-6}$ alkyl.

In certain embodiments of a method using a compound of Formula (I), $R^5$ is chosen from methyl, n-propyl, isopropyl, n-butyl, sec-butyl, isobutyl, and tert-butyl.

In certain embodiments of a method using a compound of Formula (I), $R^5$ is chosen from methyl, ethyl, n-propyl, isopropyl, n-butyl, sec-butyl, isobutyl, and tert-butyl.

In certain embodiments of a method using a compound of Formula (I), one of $R^1$ and $R^2$ is hydrogen and the other of $R^1$ and $R^2$ is $C_{1-6}$ alkyl; $R^3$ is hydrogen; $R^4$ is chosen from hydrogen, $C_{1-6}$ alkyl, and benzyl.

In certain embodiments of a method using a compound of Formula (I), one of $R^1$ and $R^2$ is hydrogen and the other of $R^1$ and $R^2$ is $C_{1-6}$ alkyl; $R^3$ is hydrogen; $R^4$ is chosen from hydrogen, $C_{1-6}$ alkyl, and benzyl; and $R^5$ is methyl.

In certain embodiments of a method using a compound of Formula (I), one of $R^1$ and $R^2$ is hydrogen and the other of $R^1$ and $R^2$ is chosen from hydrogen and $C_{1-6}$ alkyl; and each of $R^3$ and $R^4$ is $C_{1-6}$ alkyl.

In certain embodiments of a method using a compound of Formula (I), one of $R^1$ and $R^2$ is hydrogen and the other of $R^1$ and $R^2$ is chosen from hydrogen and $C_{1-6}$ alkyl; each of $R^3$ and $R^4$ is $C_{1-6}$ alkyl; and $R^5$ is methyl. In certain embodiments of a compound of Formula (I), each of $R^1$ and $R^2$ is hydrogen; each of $R^3$ and $R^4$ is $C_{1-6}$ alkyl; and $R^5$ is methyl.

In certain embodiments of a method using a compound of Formula (I), one of $R^1$ and $R^2$ is hydrogen and the other of $R^1$ and $R^2$ is chosen from hydrogen and $C_{1-4}$ alkyl; $R^3$ is hydrogen; $R^4$ is chosen from $C_{1-4}$ alkyl, substituted $C_{1-4}$ alkyl wherein the substituent group is chosen from =O, —$OR^{11}$, —$COOR^{11}$, and —$NR^{11}_2$, wherein each $R^{11}$ is independently chosen form hydrogen and $C_{1-4}$ alkyl; and $R^5$ is methyl. In certain embodiments of a method using a compound of Formula (I), one of $R^1$ and $R^2$ is hydrogen and the other of $R^1$ and $R^2$ is methyl; $R^3$ is hydrogen; $R^4$ is chosen from $C_{1-4}$ alkyl, substituted $C_{1-4}$ alkyl wherein the substituent group is chosen from =O, —$OR^{11}$, —$COOR^{11}$, and —$NR^{11}_2$, wherein each $R^{11}$ is independently chosen form hydrogen and $C_{1-4}$ alkyl; and $R^5$ is methyl. In certain embodiments of a method using a compound of Formula (I), each of $R^1$ and $R^2$ is hydrogen; $R^3$ is hydrogen; $R^4$ is chosen from $C_{1-4}$ alkyl, substituted $C_{1-4}$ alkyl wherein the substituent group is chosen from =O, —$OR^{11}$, —$COOR^{11}$, and —$NR^{11}_2$, wherein each $R^{11}$ is independently chosen form hydrogen and $C_{1-4}$ alkyl; and $R^5$ is methyl.

In certain embodiments of a method using a compound of Formula (I), $R^3$ and $R^4$ together with the nitrogen to which they are bonded form a $C_{5-10}$ heterocycloalkyl ring.

In certain embodiments of a method using a compound of Formula (I), one of $R^1$ and $R^2$ is hydrogen and the other of $R^1$ and $R^2$ is chosen from hydrogen and $C_{1-6}$ alkyl; $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring; and $R^5$ is methyl. In certain embodiments of a method using a compound of Formula (I), one of $R^1$ and $R^2$ is hydrogen and the other of $R^1$ and $R^2$ is methyl; $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring; and $R^5$ is methyl. In certain embodiments of a method using a compound of Formula (I), each of $R^1$ and $R^2$ is hydrogen; $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring; and $R^5$ is methyl.

In certain embodiments of a method using a compound of Formula (I), one of $R^1$ and $R^2$ is hydrogen and the other of $R^1$ and $R^2$ is chosen from hydrogen and $C_{1-6}$ alkyl; and $R^3$ and $R^4$ together with the nitrogen to which they are bonded form a ring chosen from morpholine, piperazine, and N-substituted piperazine.

In certain embodiments of a method using a compound of Formula (I), one of $R^1$ and $R^2$ is hydrogen and the other of $R^1$ and $R^2$ is chosen from hydrogen and $C_{1-6}$ alkyl; $R^3$ and $R^4$ together with the nitrogen to which they are bonded form a ring chosen from morpholine, piperazine, and N-substituted piperazine; and $R^5$ is methyl.

In certain embodiments of a method using a compound of Formula (I), $R^5$ is not methyl.

In certain embodiments of a method using a compound of Formula (I), $R^1$ is hydrogen, and in certain embodiments, $R^2$ is hydrogen.

In certain embodiments of a method using a compound of Formula (I), the compound is chosen from:

(N,N-diethylcarbamoyl)methyl methyl (2E)but-2-ene-1,4-dioate;
methyl [N-benzylcarbamoyl]methyl (2E)but-2-ene-1,4-dioate;
methyl 2-morpholin-4-yl-2-oxoethyl (2E)but-2-ene-1,4-dioate;
(N-butylcarbamoyl)methyl methyl (2E)but-2-ene-1,4-dioate;
[N-(2-methoxyethyl)carbamoyl]methyl methyl (2E)but-2-ene-1,4-dioate;
2-{2-[(2E)-3-(methoxycarbonyl)prop-2-enoyloxy]acetylamino}acetic acid;
4-{2-[(2E)-3-(methoxycarbonyl)prop-2-enoyloxy]acetylamino}butanoic acid;
methyl(N-(1,3,4-thiadiazol-2-yl)carbamoyl)methyl(2E)but-2ene-1,4-dioate;
(N,N-dimethylcarbamoyl)methyl methyl (2E)but-2-ene-1,4-dioate;
(N-methoxy-N-methylcarbamoyl)methyl methyl (2E)but-2-ene-1,4-dioate;
[bis-(2-methoxyethylamino)carbamoyl]methyl methyl (2E)but-2-ene-1,4-dioate;
[N-(methoxycarbonyl)carbamoyl]methyl methyl (2E)but-2ene-1,4-dioate;
4-{2-[(2E)-3-(methoxycarbonyl)prop-2-enoyloxy]acetylamino}butanoic acid, sodium salt;
methyl 2-oxo-2-piperazinylethyl (2E)but-2-ene-1,4-dioate;
methyl 2-oxo-2-(2-oxo(1,3-oxazolidin-3-yl)ethyl (2E)but-2ene-1,4-dioate;
{N-[2-(dimethylamino)ethyl]carbamoyl}methyl methyl (2E)but-2ene-1,4 dioate;
methyl 2-(4-methylpiperazinyl)-2-oxoethyl (2E)but-2-ene-1,4-dioate;
methyl {N-[(propylamino)carbonyl]carbamoyl}methyl (2E)but-2ene-1,4-dioate;
2-(4-acetylpiperazinyl)-2-oxoethyl methyl (2E)but-2ene-1,4-dioate;
{N,N-bis[2-(methylethoxy)ethyl]carbamoyl}methyl methyl (2E)but-2-ene-1,4-dioate;
methyl 2-(4-benzylpiperazinyl)-2-oxoethyl (2E)but-2-ene-1,4-dioate;
[N,N-bis(2-ethoxyethyl)carbamoyl]methyl methyl (2E)but-2-ene-1,4-dioate;
2-{(2S)-2-[(tert-butyl)oxycarbonyl]pyrrolidinyl}-2-oxoethyl methyl (2E)but-2ene-1,4-dioate;
1-{2-[(2E)-3-(methoxycarbonyl)prop-2-enoyloxy]acetyl}(2S)pyrrolidine-2-carboxylic acid;
(N-{[tert-butyl)oxycarbonyl]methyl}-N-methylcarbamoyl)methyl methyl (2E)but-2ene-1,4-dioate;
{N-(ethoxycarbonyl)methyl]-N-methylcarbamoyl}methyl methyl (2E)but-2-ene-1,4-dioate;
methyl 1-methyl-2-morpholin-4-yl-2-oxoethyl (2E)but-2-ene-1,4-dioate;
[N,N-bis(2-methoxyethyl)carbamoyl]ethyl methyl (2E)but-2-ene-1,4-dioate;
(N,N-dimethylcarbamoyl)ethyl methyl (2E)but-2-ene-1,4-dioate;
2-{2-[(2E)-3-(methoxycarbonyl)prop-2-enoyloxyl]-N-methylacetylamino}acetic acid;
(N-{[(tert-butyl)oxycarbonyl]methyl}carbamoyl)methyl methyl (2E)but-2-ene-1,4-dioate;
methyl (N-methyl-N-{[(methylethyl)oxycarbonyl]methyl}carbamoyl)methyl (2E)but-2-ene-1,4-dioate;
{N-[(ethoxycarbonyl)methyl]-N-benzylcarbamoyl}methyl methyl (2E)but-2-ene-1,4-dioate;
{N-[(ethoxycarbonyl)methyl]-N-benzylcarbamoyl}ethyl methyl (2E)but-2-ene-1,4-dioate;
{N-[(ethoxycarbonyl)methyl]-N-methylcarbamoyl}ethyl methyl (2E)but-2-ene-1,4-dioate;
(1S)-1-methyl-2-morpholin-4-yl-2-oxoethyl methyl (2E)but-2-ene-1,4-dioate;
(1S)-1-[N,N-bis(2-methoxyethyl)carbamoyl]ethyl methyl (2E)but-2-ene-1,4-dioate;

(1R)-1-(N,N-diethylcarbamoyl)ethyl methyl (2E)but-2-ene-1,4-dioate; and
a pharmaceutically acceptable salt of any of the foregoing.

In certain embodiments of a method using a compound of Formula (I), the compound is chosen from:
(N,N-diethylcarbamoyl)methyl methyl (2E)but-2-ene-1,4-dioate;
methyl [N-benzylcarbamoyl]methyl (2E)but-2-ene-1,4-dioate;
methyl 2-morpholin-4-yl-2-oxoethyl (2E)but-2-ene-1,4-dioate;
(N-butylcarbamoyl)methyl methyl (2E)but-2-ene-1,4-dioate;
[N-(2-methoxyethyl)carbamoyl]methyl methyl (2E)but-2-ene-1,4-dioate;
2-{2-[(2E)-3-(methoxycarbonyl)prop-2-enoyloxy]acetylamino}acetic acid;
{2-[(2E)-3-(methoxycarbonyl)prop-2-enoyloxy]acetylamino}butanoic acid;
methyl(N-(1,3,4-thiadiazol-2-yl)carbamoyl)methyl(2E)but-2ene-1,4-dioate;
(N,N-dimethylcarbamoyl)methyl methyl (2E)but-2-ene-1,4-dioate;
(N-methoxy-N-methylcarbamoyl)methyl methyl (2E)but-2-ene-1,4-dioate;
bis-(2-methoxyethylamino)carbamoyl]methyl methyl (2E)but-2-ene-1,4-dioate;
[N-(methoxycarbonyl)carbamoyl]methyl methyl (2E)but-2ene-1,4-dioate;
methyl 2-oxo-2-piperazinylethyl (2E)but-2-ene-1,4-dioate;
methyl 2-oxo-2-(2-oxo(1,3-oxazolidin-3-yl)ethyl (2E)but-2ene-1,4-dioate;
{N-[2-(dimethylamino)ethyl]carbamoyl}methyl methyl (2E)but-2ene-1,4 dioate;
(N-[(methoxycarbonyl)ethyl]carbamoyl)methyl methyl (2E)but-2-ene-1,4-dioate;
2-{2-[(2E)-3-(methoxycarbonyl)prop-2-enoyloxy]acetylamino}propanoic acid; and
a pharmaceutically acceptable salt of any of the foregoing.

In certain embodiments of a methods disclosed herein use an compound of Formula (I), $R^3$ and $R^4$ are independently chosen from hydrogen, $C_{1-6}$ alkyl, substituted $C_{1-6}$ alkyl, $C_{6-10}$ aryl, substituted $C_{6-10}$ aryl, $C_{4-12}$ cycloalkylalkyl, substituted $C_{4-12}$ cycloalkylalkyl, $C_{7-12}$ arylalkyl, substituted $C_{7-12}$ arylalkyl, $C_{1-6}$ heteroalkyl, substituted $C_{1-6}$ heteroalkyl, $C_{6-10}$ heteroaryl, substituted $C_{6-10}$ heteroaryl, $C_{4-12}$ heterocycloalkylalkyl, substituted $C_{4-12}$ heterocycloalkylalkyl, $C_{7-12}$ heteroarylalkyl, substituted $C_{7-12}$ heteroarylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl.

Certain embodiments of a methods disclosed herein use an compound of Formula (II):

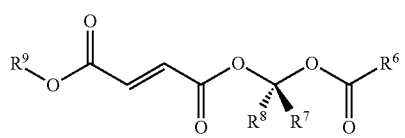

(II)

or a pharmaceutically acceptable salt thereof, wherein:
$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and $-OR^{10}$ wherein $R^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl;

$R^7$ and $R^8$ are independently chosen from hydrogen, $C_{1-6}$ alkyl, and substituted $C_{1-6}$ alkyl; and
$R^9$ is chosen from $C_{1-6}$ alkyl and substituted $C_{1-6}$ alkyl;
wherein each substituent group is independently chosen from halogen, —OH, —CN, —CF$_3$, =O, —NO$_2$, benzyl, —C(O)NR$^{11}_2$, —R$^{11}$, —OR$^{11}$, —C(O)R$^{11}$, COOR$^{11}$, and —NR$^{11}_2$ wherein each $R^{11}$ is independently chosen from hydrogen and $C_{1-4}$ alkyl.

In certain embodiments of a method using a compound of Formula (II), each substituent group is independently chosen from halogen, —OH, —CN, —CF$_3$, —R$^{11}$, —OR$^{11}$, and —NR$^{11}_2$ wherein each $R^{11}$ is independently chosen from hydrogen and $C_{1-4}$ alkyl.

In certain embodiments of a method using a compound of Formula (I), each substituent group is independently chosen from =O, $C_{1-4}$ alkyl, and —COOR$^{11}$ wherein $R^{11}$ is chosen from hydrogen and $C_{1-4}$ alkyl.

In certain embodiments of a method using a compound of Formula (II), one of $R^7$ and $R^8$ is hydrogen and the other of $R^7$ and $R^8$ is $C_{1-6}$ alkyl. In certain embodiments of a method using a compound of Formula (II), one of $R^7$ and $R^8$ is hydrogen and the other of $R^7$ and $R^8$ is $C_{1-4}$ alkyl.

In certain embodiments of a method using a compound of Formula (II), one of $R^7$ and $R^8$ is hydrogen and the other of $R^7$ and $R^8$ is chosen from methyl, ethyl, n-propyl, and isopropyl. In certain embodiments of a method using a compound of Formula (II), each of $R^7$ and $R^8$ is hydrogen.

In certain embodiments of a method using a compound of Formula (II), $R^9$ is chosen from substituted $C_{1-6}$ alkyl and —OR$^{11}$ wherein $R^{11}$ is independently $C_{1-4}$ alkyl.

In certain embodiments of a method using a compound of Formula (II), $R^9$ is $C_{1-6}$ alkyl, in certain embodiments, $R^9$ is $C_{1-3}$ alkyl; and in certain embodiments, $R^9$ is chosen from methyl and ethyl.

In certain embodiments of a method using a compound of Formula (II), $R^9$ is methyl.

In certain embodiments of a method using a compound of Formula (II), $R^9$ is chosen from ethyl, n-propyl, isopropyl, n-butyl, sec-butyl, isobutyl, and tert-butyl.

In certain embodiments of a method using a compound of Formula (II), $R^9$ is chosen from methyl, ethyl, n-propyl, isopropyl, n-butyl, isobutyl, and tert-butyl.

In certain embodiments of a method using a compound of Formula (II), $R^6$ is $C_{1-6}$ alkyl; one of $R^7$ and $R^8$ is hydrogen and the other of $R^7$ and $R^8$ is $C_{1-6}$ alkyl; and $R^9$ is chosen from $C_{1-6}$ alkyl and substituted $C_{1-6}$ alkyl.

In certain embodiments of a method using a compound of Formula (II), $R^6$ is —OR$^{10}$.

In certain embodiments of a method using a compound of Formula (II), $R^{10}$ is chosen from $C_{1-4}$ alkyl, cyclohexyl, and phenyl.

In certain embodiments of a method using a compound of Formula (II), $R^6$ is chosen from methyl, ethyl, n-propyl, and isopropyl; one of $R^7$ and $R^8$ is hydrogen and the other of $R^7$ and $R^8$ is chosen from methyl, ethyl, n-propyl, and isopropyl.

In certain embodiments of a method using a compound of Formula (II), $R^6$ is substituted $C_{1-2}$ alkyl, wherein each of the one or more substituent groups are chosen from —COOH, —NHC(O)CH$_2$NH$_2$, and —NH$_2$.

In certain embodiments of a method using a compound of Formula (II), $R^6$ is chosen from ethoxy, methylethoxy, isopropyl, phenyl, cyclohexyl, cyclohexylloxy, —CH(NH$_2$)CH$_2$COOH, —CH$_2$CH(NH$_2$)COOH, —CH(NHC(O)CH$_2$NH$_2$)—CH$_2$COOH, and —CH$_2$CH(NHC(O)CH$_2$NH$_2$)—COOH.

19

In certain embodiments of a method using a compound of Formula (II), $R^9$ is chosen from methyl and ethyl; one of $R^7$ and $R^8$ is hydrogen and the other of $R^7$ and $R^8$ is chosen from hydrogen, methyl, ethyl, n-propyl, and isopropyl; and $R^6$ is chosen from $C_{1-3}$ alkyl, substituted $C_{1-2}$ alkyl wherein each of the one or more substituent groups are chosen —COOH, —NHC(O)CH$_2$NH$_2$, and —NH$_2$, —OR$^{10}$ wherein $R^{10}$ is chosen from $C_{1-3}$ alkyl and cyclohexyl, phenyl, and cyclohexyl.

In certain embodiments of a method using a compound of Formula (II), the compound is chosen from:
ethoxycarbonyloxyethyl methyl (2E)but-2-ene-1,4-dioate;
methyl (methylethoxycarbonyloxy)ethyl (2E)but-2-ene-1,4-dioate;
(cyclohexyloxycarbonyloxy)ethyl methyl (2E)but-2-ene-1,4-dioate; and
a pharmaceutically acceptable salt of any of the foregoing.

In certain embodiments of a method using a compound of Formula (II), the compound is chosen from:
methyl (2-methylpropanoyloxy)ethyl (2E)but-2-ene-1,4-dioate;
methyl phenylcarbonyloxyethyl (2E)but-2-ene-1,4-dioate;
cyclohexylcarbonyloxybutyl methyl (2E)but-2-ene-1,4-dioate;
[(2E)-3-(methoxycarbonyl)prop-2-enoyloxy]ethyl methyl (2E)but-2-ene-1,4-dioate;
methyl 2-methyl-1-phenylcarbonyloxypropyl (2E)but-2-ene-1,4-dioate; and
a pharmaceutically acceptable salt of any of the foregoing.

In certain embodiments of a method using a compound of Formula (II), the compound is chosen from:
ethoxycarbonyloxyethyl methyl (2E)but-2-ene-1,4-dioate;
methyl (methylethoxycarbonyloxy)ethyl (2E)but-2-ene-1,4-dioate;
methyl (2-methylpropanoyloxy)ethyl (2E)but-2-ene-1,4-dioate;
methyl phenylcarbonyloxyethyl (2E)but-2-ene-1,4-dioate;
cyclohexylcarbonyloxybutyl methyl (2E)but-2-ene-1,4-dioate;
[(2E)-3-(methoxycarbonyl)prop-2-enoyloxy]ethyl methyl (2E)but-2-ene-1,4-dioate;
(cyclohexyloxycarbonyloxy)ethyl methyl (2E)but-2-ene-1,4-dioate;
methyl 2-methyl-1-phenylcarbonyloxypropyl (2E)but-2-ene-1,4-dioate;
3-({[(2E)-3-(methoxycarbonyl)prop-2-enoyloxy]methyl}oxycarbonyl)(3S)-3-aminopropanoic acid, 2,2,2-trifluoroacetic acid;
3-({[(2E)-3-(methoxycarbonyl)prop-2-enoyloxy]methyl}oxycarbonyl)(2S)-2-aminopropanoic acid, 2,2,2-trifluoroacetic acid;
3-({[(2E)-3-(methoxycarbonyl)prop-2-enoyloxy]methyl}oxycarbonyl)(3S)-3-(2-aminoacetylamino)propanoic acid, 2,2,2-trifluoroacetic acid;
3-({[(2E)-3-(methoxycarbonyl)prop-2-enoyloxy]methyl}oxycarbonyl)(2S)-2-aminopropanoic acid, 2,2,2-trifluoroacetic acid;
3-{[(2E)-3-(methoxycarbonyl)prop-2enoyloxy]ethoxycarbonyloxy}(2S)-2-aminopropanoic acid, chloride; and
a pharmaceutically acceptable salt of any of the foregoing.

Methods disclosed herein use compounds of Formula (III) and Formula (IV). Compounds of Formula (III) and Formula (IV) may be produced by in vivo metabolism of compounds of Formula (I) and Formula (II), respectively; or may be administered to a subject.

20

Accordingly, certain embodiments of methods disclosed herein use an compound of Formula (III):

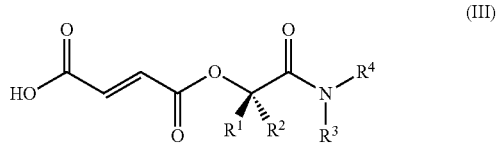

or a pharmaceutically acceptable salt thereof, wherein:
$R^1$ and $R^2$ are independently chosen from hydrogen, $C_{1-6}$ alkyl, and substituted $C_{1-6}$ alkyl; and
$R^3$ and $R^4$ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl;
wherein each substituent group is independently chosen from halogen, —OH, —CN, —CF$_3$, =O, —NO$_2$, benzyl, —C(O)NR$^{11}{}_2$, —R, —OR$^{11}$, —C(O)R$^{11}$, COOR$^{11}$, and —NR$^{11}{}_2$ wherein each $R^{11}$ is independently chosen from hydrogen and $C_{1-4}$ alkyl.

In certain embodiments of a method using a compound of Formula (III), each substituent group is independently chosen from halogen, —OH, —CN, —CF$_3$, —R$^{11}$, —OR$^{11}$, and —NR$^{11}{}_2$ wherein each $R^{11}$ is independently chosen from hydrogen and $C_{1-4}$ alkyl.

In certain embodiments of a method using a compound of Formula (III), each substituent group is independently chosen from =O, $C_{1-4}$ alkyl, and —COOR$^{11}$ wherein $R^{11}$ is chosen from hydrogen and $C_{1-4}$ alkyl.

In certain embodiments of a method using a compound of Formula (III), each of $R^1$ and $R^2$ is hydrogen.

In certain embodiments of a method using a compound of Formula (III), one of $R^1$ and $R^2$ is hydrogen and the other of $R^1$ and $R^2$ is $C_{1-4}$ alkyl.

In certain embodiments of a method using a compound of Formula (III), one of $R^1$ and $R^2$ is hydrogen and the other of $R^1$ and $R^2$ is chosen from methyl, ethyl, n-propyl, isopropyl, n-butyl, isobutyl, sec-butyl, and tert-butyl.

In certain embodiments of a method using a compound of Formula (III), one of $R^1$ and $R^2$ is hydrogen and the other of $R^1$ and $R^2$ is methyl.

In certain embodiments of a method using a compound of Formula (III), $R^3$ and $R^4$ are independently chosen from hydrogen and $C_{1-6}$ alkyl.

In certain embodiments of a method using a compound of Formula (III), $R^3$ and $R^4$ are independently chosen from hydrogen and $C_{1-4}$ alkyl.

In certain embodiments of a method using a compound of Formula (III), $R^3$ and $R^4$ are independently chosen from hydrogen, methyl, and ethyl.

In certain embodiments of a method using a compound of Formula (III), each of $R^3$ and $R^4$ is hydrogen; in certain embodiments, each of $R^3$ and $R^4$ is methyl; and in certain embodiments, each of $R^3$ and $R^4$ is ethyl.

In certain embodiments of a method using a compound of Formula (III), $R^3$ is hydrogen; and $R^4$ is chosen from $C_{1-4}$ alkyl, substituted $C_{1-4}$ alkyl wherein the substituent group is chosen from =O, —OR$^{11}$, —COOR$^{11}$, and —NR$^{11}{}_2$, wherein each $R^{11}$ is independently chosen form hydrogen and $C_{1-4}$ alkyl.

In certain embodiments of a method using a compound of Formula (III), $R^3$ is hydrogen; and $R^4$ is chosen from $C_{1-4}$ alkyl, benzyl, 2-methoxyethyl, carboxymethyl, carboxypropyl, 1,2,4-thiadoxolyl, methoxy, 2-methoxycarbonyl, 2-oxo (1,3-oxazolidinyl), 2-(methylethoxy)ethyl, 2-ethoxyethyl, (tert-butyloxycarbonyl)methyl, (ethoxycarbonyl)methyl, carboxymethyl, (methylethyl)oxycarbonylmethyl, and ethoxycarbonylmethyl.

In certain embodiments of a method using a compound of Formula (III), $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a method using a compound of Formula (III), $R^3$ and $R^4$ together with the nitrogen to which they are bonded form a ring chosen from a $C_5$ heterocycloalkyl, substituted $C_5$ heterocycloalkyl, $C_5$ heteroaryl, and substituted $C_5$ heteroaryl ring. In certain embodiments of a method using a compound of Formula (III), $R^3$ and $R^4$ together with the nitrogen to which they are bonded form a ring chosen from a $C_6$ heterocycloalkyl, substituted $C_6$ heterocycloalkyl, $C_6$ heteroaryl, and substituted $C_6$ heteroaryl ring. In certain embodiments of a method using a compound of Formula (III), $R^3$ and $R^4$ together with the nitrogen to which they are bonded form a ring chosen from piperazine, 1,3-oxazolidinyl, pyrrolidine, and morpholine ring In certain embodiments of a method using a compound of Formula (III), $R^3$ and $R^4$ together with the nitrogen to which they are bonded form a $C_{5-10}$ heterocycloalkyl ring.

In certain embodiments of a method using a compound of Formula (III), one of $R^1$ and $R^2$ is hydrogen and the other of $R^1$ and $R^2$ is $C_{1-6}$ alkyl; $R^3$ is hydrogen; $R^4$ is chosen from hydrogen, $C_{1-6}$ alkyl, and benzyl.

In certain embodiments of a method using a compound of Formula (III), one of $R^1$ and $R^2$ is hydrogen and the other of $R^1$ and $R^2$ is chosen from hydrogen and $C_{1-6}$ alkyl; and each of $R^3$ and $R^4$ is $C_{1-6}$ alkyl. In certain embodiments of a method using a compound of Formula (III), each of $R^1$ and $R^2$ is hydrogen; and each of $R^3$ and $R^4$ is $C_{1-6}$ alkyl. In certain embodiments of a method using a compound of Formula (III), one of $R^1$ and $R^2$ is hydrogen and the other of $R^1$ and $R^2$ is chosen from hydrogen and $C_{1-4}$ alkyl; $R^3$ is hydrogen; and $R^4$ is chosen from $C_{1-4}$ alkyl, substituted $C_{1-4}$ alkyl wherein the substituent group is chosen from =O, —$OR^{11}$, —$COOR^{11}$, and —$NR^{11}{}_2$, wherein each $R^{11}$ is independently chosen form hydrogen and $C_{1-4}$ alkyl. In certain embodiments of a method using a compound of Formula (III), one of $R^1$ and $R^2$ is hydrogen and the other of $R^1$ and $R^2$ is methyl; $R^3$ is hydrogen; and $R^4$ is chosen from $C_{1-4}$ alkyl, substituted $C_{1-4}$ alkyl wherein the substituent group is chosen from =O, —$OR^{11}$, —$COOR^{11}$, and —$NR^{11}{}_2$, wherein each $R^{11}$ is independently chosen form hydrogen and $C_{1-4}$ alkyl. In certain embodiments of a method using a compound of Formula (III), each of $R^1$ and $R^2$ is hydrogen; $R^3$ is hydrogen; and $R^4$ is chosen from $C_{1-4}$ alkyl, substituted $C_{1-4}$ alkyl wherein the substituent group is chosen from =O, —$OR^{11}$, —$COOR^{11}$, and —$NR^{11}{}_2$, wherein each $R^{11}$ is independently chosen form hydrogen and $C_{1-4}$ alkyl.

In certain embodiments of a method using a compound of Formula (III), $R^3$ and $R^4$ together with the nitrogen to which they are bonded form a $C_{5-10}$ heterocycloalkyl ring.

In certain embodiments of a method using a compound of Formula (III), one of $R^1$ and $R^2$ is hydrogen and the other of $R^1$ and $R^2$ is chosen from hydrogen and $C_{1-6}$ alkyl; and $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a method using a compound of Formula (III), one of $R^1$ and $R^2$ is hydrogen and the other of $R^1$ and $R^2$ is methyl; and $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a method using a compound of Formula (III), each of $R^1$ and $R^2$ is hydrogen; and $R^3$ and $R^4$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring.

In certain embodiments of a method using a compound of Formula (III), one of $R^1$ and $R^2$ is hydrogen and the other of $R^1$ and $R^2$ is chosen from hydrogen and $C_{1-6}$ alkyl; and $R^3$ and $R^4$ together with the nitrogen to which they are bonded form a ring chosen from morpholine, piperazine, and N-substituted piperazine.

In certain embodiments of a method using a compound of Formula (III), $R^3$ and $R^4$ are independently chosen from hydrogen, $C_{1-6}$ alkyl, substituted $C_{1-6}$ alkyl, $C_{6-10}$ aryl, substituted $C_{6-10}$ aryl, $C_{4-12}$ cycloalkylalkyl, substituted $C_{4-12}$ cycloalkylalkyl, $C_{7-12}$ arylalkyl, substituted $C_{7-12}$ arylalkyl, $C_{1-6}$ heteroalkyl, substituted $C_{1-6}$ heteroalkyl, $C_{6-10}$ heteroaryl, substituted $C_{6-10}$ heteroaryl, $C_{4-12}$ heterocycloalkylalkyl, substituted $C_{4-12}$ heterocycloalkylalkyl, $C_{7-12}$ heteroarylalkyl, substituted $C_{7-12}$ heteroarylalkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl.

In certain embodiments of a method using a compound of Formula (III), $R^1$ is hydrogen, and in certain embodiments, $R^2$ is hydrogen.

In certain embodiments of a method using a compound of Formula (III), the compound is chosen from:
(2E)-3-[(2-morpholin-4-yl-2-oxoethyl)oxycarbonyl]prop-2-enoic acid;
(2E)-3-{[(N,N-diethylcarbamoyl)methyl]oxycarbonyl}prop-2-enoic acid;
(2E)-3-({[N-benzylcarbamoyl]methyl}oxycarbonyl)prop-2-enoic acid;
(2E)-3-[(2-morpholin-4-yl-2-oxoethyl)oxycarbonyl]prop-2-enoic acid;
(2E)-3-{[(N-butylcarbamoyl)methyl]oxycarbonyl}prop-2-enoic acid;
(2E)-3-{[N-methoxy-N-methylcarbamoyl)methyl]oxycarbonyl}prop-2-enoic acid;
bis-(2-methoxyethylamino)carbamoyl]methyl prop-2-enoic acid;
N,N-dimethylcarbamoyl)methyl pro-2-enoic acid;
(2E)-3-({[N-(3-carboxypropyl)carbamoyl]methyl}oxycarbonyl)prop-2-enoic acid;
methyl (N-(1,3,4-thiadiazol-2-yl)carbamoyl)methyl prop-2-enoic acid;
(2E)-3-[(2-{(2S)-2-[tert-butyl)oxycarbonyl]pyrrolidinyl}-2-oxoethyl) oxycarbonyl]prop-2enoic acid;
1-[2-((2E)-3-carboxyprop-2-enoyloxy)acetyl](2S) pyrrolidine-2-carboxylic acid;
(2E)-3-[([N-[(ethoxycarbonyl)methyl]-N-methylcarbamoyl}methyl)oxycarbonyl]prop-2-enoic acid;
(2E)-3-{[N-{[(tert-butyl)oxycarbonyl]methyl}-N-methylcarbamoyl)methyl]oxycarbonyl}prop-2-enoic acid;
(2E)-3-[(1-methyl-2-morpholin-4-yl-2-oxoethyl)oxycarbonyl]prop-2-enoic acid;

(2E)-3-({[N,N-bis(2-methoxyethyl)carbamoyl]
ethyl}oxycarbonyl)prop-2-enoic acid;
(2E)-3-{[(N,N-dimethylcarbamoyl)ethyl]
oxycarbonyl}prop-2-enoic acid;
(2E)-3-[({N,N-bis[2-methylethoxy)ethyl]
carbamoyl}methyl)oxycarbonyl]prop-2-enoic acid;
(2E)-3-({[N,N-bis(2-ethoxyethyl)carbamoyl]
methyl}oxycarbonyl)prop-2-enoic acid;
(2E)-3-{[2-(4-acetylpiperazinyl)-2-oxoethyl]
oxycarbonyl}prop-2-enoic acid;
(2E)-3-({2-oxo-2-[4-benzylpiperazinyl]ethyl}oxycarbonyl)
prop-2-enoic acid;
(2E)-3-{[(N-{[(tert-butyl)oxycarbonyl]methyl}carbamoyl)
methyl]oxycarbonyl}prop-2-enoic acid;
(2E)-3-{[(N-methyl-N-{[(methylethyl)oxycarbonyl]
methyl}carbamoyl)methyl]oxycarbonyl}prop-2-enoic
acid;
(2E)-3-[({N-[(ethoxycarbonyl)methyl]-N-
benzylcarbamoyl}methyl)oxycarbonyl]prop-2-enoic
acid;
(2E)-3-[({N-[(ethoxycarbonyl)methyl]-N-
benzoyarbamoyl}ethyl)oxycarbonyl]prop-2-enoic acid;
(2E)-3-[({N-[(ethoxycarbonyl)methyl]-N-
methylcarbamoyl}ethyl)oxycarbonyl]prop-2-enoic acid;
and
a pharmaceutically acceptable salt of any of the foregoing.

Certain embodiments of methods disclosed herein use an
compound of Formula (IV):

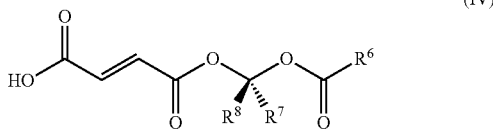

(IV)

or a pharmaceutically acceptable salt thereof, wherein:
$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —$OR^{10}$, wherein $R^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl; and $R^7$ and $R^8$ are independently chosen from hydrogen, $C_{1-6}$ alkyl, and substituted $C_{1-6}$alkyl; wherein each substituent group is independently chosen from halogen, —OH, —CN, —$CF_3$, =O, —$NO_2$, benzyl, —$C(O)NR^{11}{}_2$, —$R^{11}$, $OR^{11}$, —$C(O)R^{11}$, —$COOR^{11}$, and —$NR^{11}{}_2$ wherein each $R^{11}$ is independently chosen from hydrogen and $C_{1-4}$ alkyl;

with the provisos that; when one of $R^7$ and $R^8$ is chosen from ethyl and methyl, and the other of $R^7$ and $R^8$ is hydrogen; then $R^6$ is not —$C(CH_3)$=$CH_2$; and when each of $R^7$ and $R^8$ is hydrogen; then $R^6$ is not chosen from —CH=$CH_2$ and 4-carboxyphenyl.

In certain embodiments of a method using a compound of Formula (IV), each substituent group is independently chosen from halogen, —OH, —CN, —$CF_3$, —$R^{11}$, —$OR^{11}$, and —$NR^{11}{}_2$ wherein each $R^{11}$ is independently chosen from hydrogen and $C_{1-4}$ alkyl.

In certain embodiments of a method using a compound of Formula (IV), each substituent group is independently chosen from =O, $C_{1-4}$ alkyl, and —$COOR^{11}$ wherein $R^{11}$ is chosen from hydrogen and $C_{1-4}$ alkyl.

In certain embodiments of a method using a compound of Formula (IV), one of $R^7$ and $R^8$ is hydrogen and the other of $R^7$ and $R^8$ is $C_{1-6}$ alkyl. In certain embodiments of a method using a compound of Formula (IV), one of $R^7$ and $R^8$ is hydrogen and the other of $R^7$ and $R^8$ is $C_{1-4}$ alkyl.

In certain embodiments of a method using a compound of Formula (IV), one of $R^7$ and $R^8$ is hydrogen and the other of $R^7$ and $R^8$ is chosen from methyl, ethyl, n-propyl, and isopropyl. In certain embodiments of a method using a compound of Formula (IV), each of $R^7$ and $R^8$ is hydrogen.

In certain embodiments of a method using a compound of Formula (IV), $R^6$ is $C_{1-6}$ alkyl; and one of $R^7$ and $R^8$ is hydrogen and the other of $R^7$ and $R^8$ is $C_{1-6}$ alkyl.

In certain embodiments of a method using a compound of Formula (IV), $R^6$ is —$OR^{10}$.

In certain embodiments of a method using a compound of Formula (IV), $R^{10}$ is chosen from $C_{1-4}$ alkyl, cyclohexyl, and phenyl.

In certain embodiments of a method using a compound of Formula (IV), $R^6$ is chosen from methyl, ethyl, n-propyl, and isopropyl; one of $R^7$ and $R^8$ is hydrogen and the other of $R^7$ and $R^8$ is chosen from methyl, ethyl, n-propyl, and isopropyl.

In certain embodiments of a method using a compound of Formula (IV), $R^6$ is substituted $C_{1-2}$ alkyl, wherein each of the one or more substituent groups are chosen from —COOH, —$NHC(O)CH_2NH_2$, and —$NH_2$.

In certain embodiments of a method using a compound of Formula (IV), $R^6$ is chosen from ethoxy, methylethoxy, isopropyl, phenyl, cyclohexyl, cyclohexyloxy, —$CH(NH_2)CH_2COOH$, —$CH_2CH(NH_2)COOH$, —$CH(NHC(O)CH_2NH_2)$—$CH_2COOH$, and —$CH_2CH(NHC(O)CH_2NH_2)$—COOH.

In certain embodiments of a method using a compound of Formula (IV), one of $R^7$ and $R^8$ is hydrogen and the other of $R^7$ and $R^8$ is chosen from hydrogen, methyl, ethyl, n-propyl, and isopropyl; and $R^6$ is chosen from $C_{1-3}$ alkyl, substituted $C_{1-2}$ alkyl wherein each of the one or more substituent groups are chosen —COOH, —$NHC(O)CH_2NH_2$, and —$NH_2$, —$OR^{10}$ wherein $R^{10}$ is chosen from $C_{1-3}$ alkyl and cyclohexyl, phenyl, and cyclohexyl.

In certain embodiments of a method using a compound of Formula (IV), the compound is chosen from:
(2E)-3-{[(2-methylpropanoyloxy)ethyl]oxycarbonyl}prop-2-enoic acid;
(2E)-3-({[(methylethyl)oxycarbonyloxy]
ethyl}oxycarbonyl)prop-2-enoic acid;
2-[(2E)-3-(methoxycarbonyl)prop-2-enoyloxy]acetic acid; and
a pharmaceutically acceptable salt of any of the foregoing.

Synthesis

Prodrug compounds of Formula I, II, III or IV disclosed herein may be obtained via the synthetic methods illustrated in U.S. Pat. No. 8,148,414, the Gangakhedkar disclosure of which are incorporated herein by reference. General synthetic methods useful in the synthesis of compounds described herein are available in the art. Starting materials useful for preparing compounds and intermediates thereof and/or practicing methods described herein are commercially available or can be prepared by well-known synthetic methods. It will be apparent to those skilled in the art that many modifications, both to materials and methods, may be practiced without departing from the scope of the disclosure.

Pharmaceutical Composition

Pharmaceutical compositions provided by the present disclosure may comprise a therapeutically effective amount of a compound of Formulae (I)-(IV) together with a suitable amount of one or more pharmaceutically acceptable vehicles so as to provide a composition for proper administration to a subject. Suitable pharmaceutical vehicles are described in the art.

In certain embodiments, a compound of Formulae (I)-(IV) may be incorporated into pharmaceutical compositions to be administered orally. Oral administration of such pharmaceutical compositions may result in uptake of a compound of Formulae (I)-(IV) throughout the intestine and entry into the systemic circulation. Such oral compositions may be prepared in a manner known in the pharmaceutical art and comprise a compound of Formulae (I)-(IV) and at least one pharmaceutically acceptable vehicle. Oral pharmaceutical compositions may include a therapeutically effective amount of a compound of Formulae (I)-(IV) and a suitable amount of a pharmaceutically acceptable vehicle, so as to provide an appropriate form for administration to a subject.

Compounds of Formulae (I)-(IV) may be incorporated into pharmaceutical compositions to be administered by any other appropriate route of administration including intradermal, intramuscular, intraperitoneal, intravenous, subcutaneous, intranasal, epidural, oral, sublingual, intracerebral, intravaginal, transdermal, rectal, inhalation, or topical.

Pharmaceutical compositions comprising a compound of Formulae (I)-(IV) and may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formulae (I)-(IV) or crystalline forms thereof and one or more pharmaceutically acceptable vehicles into formulations that can be used pharmaceutically. Proper formulation is dependent upon the route of administration chosen. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a subject.

Pharmaceutical compositions provided by the present disclosure may be formulated in a unit dosage form. A unit dosage form refers to a physically discrete unit suitable as a unitary dose for subjects undergoing treatment, with each unit containing a predetermined quantity of a compound of Formulae (I)-(IV) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a subject at a single point in time or during a time interval.

Pharmaceutical compositions comprising a compound of Formulae (I)-(IV) may be formulated for immediate release.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of a compound of Formulae (I)-(IV) the stability of a compound of Formulae (I)-(IV) in the gastrointestinal tract, the pharmacokinetics of a compound of Formulae (I)-(IV) and the intended therapeutic profile. An appropriate controlled release oral dosage form may be selected for a particular compound of Formulae (I)-(IV). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of a compound of Formulae (I)-(IV) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

An appropriate dose of a compound of Formulae (I)-(IV) or pharmaceutical composition comprising a compound of Formulae (I)-(IV) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses

Compounds of Formulae (I)-(IV) are prodrugs of MHF. Thus, compounds of Formulae (I)-(IV) and pharmaceutical compositions thereof may be administered to a subject suffering from any disease including a disorder, condition, or symptom for which MHF is known or hereafter discovered to be therapeutically effective. The present disclosure provides, in part, methods for the treatment of a heart failure disease by administering to a subject in need thereof, a therapeutically effective amount of a compound of Formula (I), (II), (III) or (IV), or a pharmaceutically acceptable salt, polymorph, hydrate, solvate or co-crystal thereof.

In one embodiment, the heart failure disease may be heart failure with preserved ejection fraction (HFPEF); heart failure with ejection fraction ≥40%; diastolic heart failure; heart failure with elevated levels of TNF-α, IL-6, CRP, or TGF-β; hypertension with a risk of developing HFPEF; atrial fibrillation with a risk of developing HFPEF; diabetes with a risk of developing HFPEF; COPD with a risk of developing HFPEF; ischemic heart disease with a risk of developing HFPEF; obesity with a risk of developing HFPEF; chronic heart failure; compensated heart failure; decompensated heart failure; or other conditions known to have a high risk of developing HFPEF. In particular, heart failure disease is heart failure with preserved ejection fraction (HFPEF). The present disclosure further provides the use of a compound of Formula (I), (II), (III) or (IV), or a pharmaceutically acceptable salt, polymorph, hydrate, solvate or co-crystal thereof, for the preparation of a medicament useful for the treatment of a heart failure disease.

In a further embodiment, the present disclosure provides methods for the treatment of a heart failure disease or a symptom of a heart failure disease described herein by administering to a subject in need thereof, a therapeutically effective amount of a compound of Formula (I), (II), (III) or (IV), or a pharmaceutically acceptable salt, polymorph, hydrate, solvate or co-crystal thereof. The present disclosure further provides the use of a compound of Formula (I), (II), (III) or (IV), or a pharmaceutically acceptable salt, polymorph, hydrate, solvate or co-crystal thereof, for the preparation of a medicament useful for the treatment of a disease or a symptom of a disease described herein.

MHF prodrugs having high gastrointestinal permeability and/or absorption, improved solubility, ordered hydrolysis (i.e., preferential cleavage of promoieties), and minimal cleavage in the gut lumen or enterocyte cytoplasm are desirable. Such MHF prodrugs that provide higher oral bioavailability and plasma levels of MHF, DMF, and/or other metabolites may enhance the efficacy/responder rate compared to present fumaric acid esters; facilitate the use of lower doses, reduced dosing frequency, and standardized dosing regimens; reduce food effects; reduce gastrointestinal side effects/toxicity; and reduce intersubject treatment variability.

In another embodiment, the present disclosure provides a method for the treatment of a heart failure disease by administering to a subject in need thereof, a therapeutically effective amount of a compound of Formula (I):

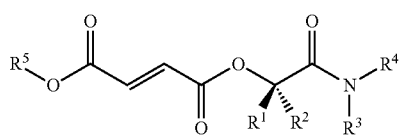

(I)

or a pharmaceutically acceptable salt thereof, wherein:

$R^1$ and $R^2$ are independently chosen from hydrogen, $C_{1-6}$ alkyl, and substituted $C_{1-6}$ alkyl;

$R^3$ and $R^4$ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ aryl-alkyl; or $R^3$ and $R^4$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and $R^5$ is chosen from methyl, ethyl, and $C_{3-6}$ alkyl;

wherein each substituent group is independently chosen from halogen, —OH, —CN, —CF$_3$, ═O, —NO$_2$, benzyl, —C(O)NR$^{11}_2$, —R, —OR$^{11}$, —C(O)R$^{11}$, COOR$^{11}$, and —NR$^{11}_2$ wherein each $R^{11}$ is independently chosen from hydrogen and $C_{1-4}$ alkyl;

with the provisos that when $R^5$ is ethyl; then $R^3$ and $R^4$ are independently chosen from hydrogen, $C_{1-6}$ alkyl, and substituted $C_{1-6}$ alkyl.

For example, the heart failure disease is HFPEF.

For example, the heart failure disease is heart failure with an ejection fraction ≥40%.

For example, the heart failure disease is diastolic heart failure.

For example, the heart failure disease is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing HFPEF.

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

In another embodiment, the present disclosure provides a method for the treatment of a heart failure disease by administering to a subject in need thereof, a therapeutically effective amount of a compound of Formula (II):

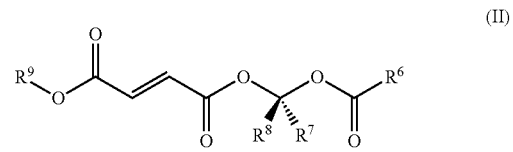

(II)

or a pharmaceutically acceptable salt thereof, wherein:

$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —OR$^{10}$ wherein $R^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl;

$R^7$ and $R^8$ are independently chosen from hydrogen, $C_{1-6}$ alkyl, and substituted $C_{1-6}$alkyl; and $R^9$ is chosen from $C_{1-6}$ alkyl and substituted $C_{1-6}$ alkyl;

wherein each substituent group is independently chosen from halogen, —OH, —CN, —CF$_3$, ═O, —NO$_2$, benzyl, —C(O)NR$^{11}_2$, —R$^{11}$, —OR$^{11}$, —C(O)R$^{11}$, COOR$^{11}$, and —NR$^{11}_2$ wherein each R$^{11}$ is independently chosen from hydrogen and C$_{1-4}$ alkyl.

For example, the heart failure disease is HFPEF.

For example, the heart failure disease is heart failure with an ejection fraction ≥40%.

For example, the heart failure disease is diastolic heart failure.

For example, the heart failure disease is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing HFPEF.

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

In another embodiment, the present disclosure provides a method for the treatment of a heart failure disease by administering to a subject in need thereof, a therapeutically effective amount of a compound of Formula (III):

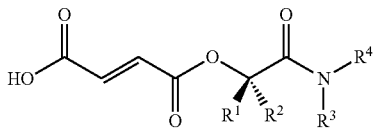

(III)

or a pharmaceutically acceptable salt thereof, wherein:

R$^1$ and R$^2$ are independently chosen from hydrogen, C$_{1-6}$ alkyl, and substituted C$_{1-6}$alkyl; and R$^3$ and R$^4$ are independently chosen from hydrogen, C$_{1-6}$ alkyl, substituted C$_{1-6}$alkyl, C$_{1-6}$ heteroalkyl, substituted C$_{1-6}$ heteroalkyl, C$_{4-12}$ cycloalkylalkyl, substituted C$_{4-12}$ cycloalkylalkyl, C$_{7-12}$ arylalkyl, and substituted C$_{7-12}$ arylalkyl; or R$^3$ and R$^4$ together with the nitrogen to which they are bonded form a ring chosen from a C$_{5-10}$ heteroaryl, substituted C$_{5-10}$ heteroaryl, C$_{5-10}$ heterocycloalkyl, and substituted C$_{5-10}$ heterocycloalkyl;

wherein each substituent group is independently chosen from halogen, —OH, —CN, —CF$_3$, =O, —NO$_2$, benzyl, —C(O)NR$^{11}_2$, —R$^{11}$, —OR$^{11}$, —C(O)R$^{11}$, —COOR$^{11}$, and —NR$^{11}_2$ wherein each R$^{11}$ is independently chosen from hydrogen and C$_{1-4}$ alkyl.

For example, the heart failure disease is HFPEF.

For example, the heart failure disease is heart failure with an ejection fraction ≥40%.

For example, the heart failure disease is diastolic heart failure.

For example, the heart failure disease is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing HFPEF.

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

In another embodiment, the present disclosure provides a method for the treatment of a heart failure disease by administering to a subject in need thereof, a therapeutically effective amount of a compound of Formula (IV):

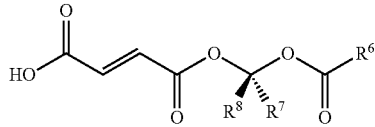

(IV)

or a pharmaceutically acceptable salt thereof, wherein:

R$^6$ is chosen from C$_{1-6}$ alkyl, substituted C$_{1-6}$ alkyl, C$_{1-6}$ heteroalkyl, substituted C$_{1-6}$ heteroalkyl, C$_{3-8}$ cycloalkyl, substituted C$_{3-8}$ cycloalkyl, C$_{6-8}$ aryl, substituted C$_{6-8}$ aryl, and —OR$^{10}$, wherein R$^{10}$ is chosen from C$_{1-6}$ alkyl, substituted C$_{1-6}$ alkyl, C$_{3-10}$ cycloalkyl, substituted C$_{3-10}$ cycloalkyl, C$_{6-10}$ aryl, and substituted C$_{6-10}$ aryl; and R$^7$ and R$^8$ are independently chosen from hydrogen, C$_{1-6}$ alkyl, and substituted C$_{1-6}$ alkyl;

wherein each substituent group is independently chosen from halogen, —OH, —CN, —CF$_3$, =O, —NO$_2$, benzyl, —C(O)NR$^{11}_2$, —R$^{11}$, —OR$^{11}$, C(O)R$^{11}$, COOR$^{11}$, and —NR$^{11}_2$ wherein each R$^{11}$ is independently chosen from hydrogen and C$_{1-4}$ alkyl;

with the provisos that; when one of R$^7$ and R$^8$ is chosen from ethyl and methyl, and the other of R$^7$ and R$^8$ is hydrogen; then R$^6$ is not —C(CH$_3$)=CH$_2$; and when each of R$^7$ and R$^8$ is hydrogen; then R$^6$ is not chosen from —CH=CH$_2$ and 4-carboxyphenyl.

For example, the heart failure disease is HFPEF.

For example, the heart failure disease is heart failure with an ejection fraction ≥40%.

For example, the heart failure disease is diastolic heart failure.

For example, the heart failure disease is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing HFPEF.

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

In another embodiment, methods of treating a disease in a subject are provided comprising administering to a subject in need of such treatment a pharmaceutical composition comprising a therapeutically effective amount of a compound of Formulae (I)-(IV). In certain embodiments, the heart failure disease may be heart failure with preserved ejection fraction (HFPEF); heart failure with ejection fraction ≥40%; diastolic heart failure; heart failure with elevated levels of TNF-α, IL-6, CRP, or TGF-β; hypertension with a risk of developing HFPEF; atrial fibrillation with a risk of developing HFPEF; diabetes with a risk of developing HFPEF; COPD with a risk of developing HFPEF; ischemic heart disease with a risk of developing HFPEF; obesity with a risk of developing HFPEF; chronic heart failure; compensated heart failure; decompensated heart failure; or other conditions known to have a high risk of developing HFPEF. In particular, heart failure disease is heart failure with preserved ejection fraction (HFPEF).

In another embodiment, methods of inhibiting NF-κB activation in a heart failure subject are provided comprising administering to a subject a pharmaceutical composition comprising a therapeutically effective amount of a compound of Formulae (I)-(IV).

In another embodiment, methods of inhibiting TNF function in a heart failure subject are provided comprising administering to a subject a pharmaceutical composition comprising a therapeutically effective amount of a compound of Formulae (I)-(IV).

Dosage and Administration

Compounds of Formulae (I)-(IV) or pharmaceutical compositions thereof may provide therapeutic or prophylactic plasma and/or blood concentrations of MHF following administration to a subject.

MHF prodrugs of Formulae (I)-(IV) may be included in a pharmaceutical composition and/or dosage form adapted for oral administration, although MHF prodrug of Formulae (I)-(IV) may also be administered by any other appropriate route, such as for example, by injection, infusion, inhalation, transdermal, or absorption through epithelial or mucosal membranes (e.g., oral, rectal, and/or intestinal mucosa).

MHF prodrugs of Formulae (I)-(IV) may be administered in an amount and using a dosing schedule as appropriate for treatment of a particular disease. Daily doses of a MHF prodrug of Formulae (I)-(IV) may range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, MHF prodrugs of Formulae (I)-(IV) may be administered at a dose over time from about 1 mg to about 5 g per day, from about 10 mg to about 4 g per day, and in certain embodiments from about 20 mg to about 2 g per day. An appropriate dose of a MHF prodrug of Formulae (I)-(IV) may be determined based on several factors, including, for example, the body weight and/or condition of the subject being treated, the severity of the disease being treated, the incidence and/or severity of side effects, the manner of administration, and the judgment of the prescribing physician. Appropriate dose ranges may be determined by methods known to those skilled in the art.

MHF prodrugs of Formulae (I)-(IV) may be assayed in vitro and in vivo for the desired therapeutic or prophylactic activity prior to use in humans. In vivo assays, for example using appropriate animal models, may also be used to determine whether administration of a MHF prodrug of Formulae (I)-(IV) is therapeutically effective.

In certain embodiments, a therapeutically effective dose of a MHF prodrug of Formulae (I)-(IV) may provide therapeutic benefit without causing substantial toxicity including adverse side effects. Toxicity of MHF prodrugs of Formulae (I)-(IV) and/or metabolites thereof may be determined using standard pharmaceutical procedures and may be ascertained by those skilled in the art. The dose ratio between toxic and therapeutic effect is the therapeutic index. A dose of a MHF prodrug of Formulae (I)-(IV) may be within a range capable of establishing and maintaining a therapeutically effective circulating plasma and/or blood concentration of a MHF prodrug of Formulae (I)-(IV) that exhibits little or no toxicity.

MHF prodrug of Formulae (I)-(IV) may be used to treat diseases, disorders, conditions, and symptoms of any heart failure condition, including heart failure with preserved ejection fraction (HFPEF). Further, in certain embodiments, a therapeutically effective amount of one or more compounds of Formulae (I)-(IV) may be administered to a subject, such as a human, as a preventative measure against various heart failure conditions, including heart failure with preserved ejection fraction (HFPEF). Thus, a therapeutically effective amount of one or more compounds of Formulae (I)-(IV) may be administered as a preventative measure to a subject having a predisposition for and/or history of a comorbidity or condition associated with heart failure with preserved ejection fraction (HFPEF), such as hypertension, diabetes, chronic obstructive pulmonary disease, atrial fibrillation, obesity, or other conditions known to increase risk of HFPEF.

MHF prodrugs of Formulae (I)-(IV) and pharmaceutical compositions thereof may be administered orally or by any other appropriate route, for example, by infusion or bolus injection, by absorption through epithelial or mucocutaneous linings (e.g., oral mucosa, rectal, and intestinal mucosa, etc.). Other suitable routes of administration include, but are not limited to, intradermal, intramuscular, intraperitoneal, intravenous, subcutaneous, intranasal, epidural, oral, sublingual, intracerebral, intravaginal, transdermal, rectal, inhalation, or topical.

Administration may be systemic or local. Various delivery systems are known, e.g., encapsulation in liposomes, microparticles, microcapsules, capsules, etc. that may be used to administer a compound and/or pharmaceutical composition.

The amount of a MHF prodrug of Formulae (I)-(IV) that will be effective in the treatment of a disease in a subject will depend, in part, on the nature of the condition and can be determined by standard clinical techniques known in the art. In addition, in vitro or in vivo assays may be employed to help identify optimal dosage ranges. A therapeutically effective amount of a MHF prodrug of Formulae (I)-(IV) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of a MHF prodrug of Formulae (I)-(IV) contained in a dose may depend on the route of administration and whether the disease in a subject is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a MHF prodrug may exhibit a high therapeutic index. The data obtained from these cell culture assays and animal studies may be used in formulating a dosage range that is not toxic for use in humans. A dose of a MHF prodrug provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

The dose will be adjusted to the individual requirements in each particular case. That dosage may vary within wide limits depending upon numerous factors such as the severity of the disease to be treated, the age and general health condition of the subject, other medicaments with which the subject is being treated, the route and form of administration, and the preferences and experience of the medical practitioner involved. For oral administration, therapeutically effective amount of (N,N-diethylcarbamoyl)methyl methyl (2E)but-2-ene-1,4-dioate or a pharmaceutically acceptable salt thereof that is shown to provide MMF plasma exposure comparable to 120 mg to 720 mg per day of dimethyl fumarate (DMF) as a monotherapy and/or in combination therapy. In one embodiment, daily dose comprises 200 mg to 1200 mg of the (N,N-diethylcarbamoyl) methyl methyl (2E)but-2-ene-1,4-dioate or a pharmaceutically acceptable salt thereof In another embodiment, the daily dose would be 400 mg BID, with the upper limit being 400 mg TID of the (N,N-diethylcarbamoyl)methyl methyl (2E)but-2-ene-1,4-dioate or a pharmaceutically acceptable salt thereof One of ordinary skill in treating diseases described herein will be able, without undue experimentation and in reliance on personal knowledge, experience and the disclosures of this application, to ascertain a therapeutically effective amount of the compounds of the present invention for a given disease and subject.

Combination Therapy

Methods provided by the present disclosure further comprise administering one or more therapeutic agent in addition to a MHF prodrug of Formulae (I)-(IV). Such compounds may be provided to treat the same disease or a different disease than the disease being treated with the MHF prodrug of Formulae (I)-(IV).

In certain embodiments, a MHF prodrug of Formulae (I)-(IV) may be used in combination with at least one other therapeutic agent. In certain embodiments, a MHF prodrug of Formulae (I)-(IV) may be administered to a subject together with another compound for treating a heart failure disease, such as HFPEF.

A MHF prodrug of Formulae (I)-(IV) and the at least one other therapeutic agent may act additively or, and in certain embodiments, synergistically. The at least one additional therapeutic agent may be included in the same dosage form as a MHF prodrug of Formulae (I)-(IV) or may be provided in a separate dosage form. Methods provided by the present disclosure can further include, in addition to administering a MHF prodrug of Formulae (I)-(IV), administering one or more therapeutic agents effective for treating the same or different disease than the disease being treated by a MHF prodrug of Formulae (I)-(IV). Methods provided by the present disclosure include administration of a MHF prodrug of Formulae (I)-(IV) and one or more other therapeutic agents provided that the combined administration does not inhibit the therapeutic efficacy of the MHF prodrug and/or does not typically produce significant and/or substantial adverse combination effects.

In certain embodiments, dosage forms comprising a MHF prodrug of Formulae (I)-(IV) may be administered concurrently with the administration of another therapeutic agent, which may be part of the same dosage form as, or in a different dosage form than that comprising a MHF prodrug of Formulae (I)-(IV). A MHF prodrug of Formulae (I)-(IV) may be administered prior or subsequent to administration of another therapeutic agent. In certain embodiments of combination therapy, the combination therapy may comprise alternating between administering a MHF prodrug of Formulae (I)-(IV) and a composition comprising another therapeutic agent, e.g., to minimize adverse drug effects associated with a particular drug. When a MHF prodrug of Formulae (I)-(IV) is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising a MHF prodrug of Formulae (I)-(IV) may be administered with one or more substances to enhance, modulate and/or control release, bioavailability, therapeutic efficacy, therapeutic potency, stability, and the like of a MHF prodrug of Formulae (I)-(IV). For example, to enhance the therapeutic efficacy of a MHF prodrug ligand of Formulae (I)-(IV), the MHF prodrug of Formulae (I)-(IV) may be co-administered with or a dosage form comprising a MHF prodrug of Formulae (I)-(IV) may comprise one or more active agents to increase the absorption or diffusion of a MHF prodrug of Formulae (I)-(IV) from the gastrointestinal tract to the systemic circulation, or to inhibit degradation of the MHF prodrug of Formulae (I)-(IV) in the blood of a subject. In certain embodiments, a MHF prodrug of Formulae (I)-(IV) may be co-administered with an active agent having pharmacological effects that enhance the therapeutic efficacy of a MHF prodrug of Formulae (I)-(IV).

In certain embodiments, administration of MHF prodrug of Formulae (I)-(IV) may also be carried out in the combination with administration of one or more preparations of a second agent useful for treating heart failure, such as but not limited to diuretics, ace-inhibitors, beta-blockers, angiotensin receptor blockers, isosorbide dinitrate, hydralazine, angiotensin receptor-neprilysin inhibitors, aldosterone antagonists, a PDE5 inhibitor, a statin, a neprilysin inhibitor, an aldosterone inhibitor, or an antitumor necrosis factor-alpha therapy. In one embodiment, the second agent is a statin, for example atorvastatin, fluvastatin, lovastatin, pravastatin, rosuvastatin, or simvastatin. For this purpose, the preparations administered may comprise a combination of the active ingredients in the known dosages or amounts, respectively.

In one embodiment, combination relates to (a) (N,N-diethylcarbamoyl)methyl methyl (2E)but-2-ene-1,4-dioate or a pharmaceutically acceptable salt thereof and (b) a statin for treatment of heart failure disease, including heart failure with preserved ejection fraction.

In some embodiments, a pharmaceutical composition is provided comprising (a) (N,N-diethylcarbamoyl)methyl methyl (2E)but-2-ene-1,4-dioate and (b) a statin.

In one embodiment, a (N,N-diethylcarbamoyl)methyl methyl (2E)but-2-ene-1,4-dioate or a pharmaceutically acceptable salt thereof is administered at a dose range of 200 mg to 1200 mg and a statin is given at a dose range of 10 mg to 80 mg for treatment of heart failure disease, including heart failure with preserved ejection fraction. In some embodiments, the statin is selected from group consisting of atorvastatin, fluvastatin, lovastatin, pravastatin, rosuvastatin, and simvastatin.

In certain embodiments, prodrugs provided by the present disclosure and pharmaceutical compositions thereof may be administered to a subject for treating heart failure with reduced ejection fraction (HFREF) in combination with a therapy or another therapeutic agent known or believed to be effective in treating HFREF. Useful drugs for treating HFREF include antitensin-modulating agents, diuretics such as furosemide, bumetanie, hydrochlorothiazide, chlorthalidone, chlorthiazide, spironolactone, eplerenone: beta blockers such as bisoprolol, carvedilol, and metroprolol; positive inotropes such as digoxin, milrinone, and dobutamine; alternative vasodilators such as isosorbide dinitrate/hydralazine; aldosterone receptor antagonists; recombinant neuroendocrine hormones such as nesiritide; angiotensin receptor-neprilysin inhibitors such as LCZ696; and vasopressin receptor antagonists such as tolvaptan and conivaptan.

PROPHETIC EXAMPLE 1

The following prophetic example serves to provide approximate dosage levels of prodrugs of methyl hydrogen fumarate to achieve the intended effect, for example treatment of heart failure with preserved ejection fraction (HFPEF). Based on the literature, a few assumptions about the dosage can be made, as will be described in further detail below.

The full mechanism of fumaric acid esters such as dimethyl fumarate (DMF) and its primary metabolite, monomethyl fumarate (MMF), is not completely understood, but their beneficial effects appear to be mediated, at least in part, through the activation of the NRF2 antioxidant response pathway, which further increases expression of antioxidant respose element (ARE), which increases expression of detoxifying enzymes and antioxidant proteins.

NRF2 deficiency, demonstrated by NRF2 knockout in murine models, results in an earlier onset of cardiac dysfunction induced by pressure and volume overload (Li et al Arterioscler Thromb Vasc Biol. 2009, 29(11), 1843-50).

Certain NRF2 activators such as sulforaphane, curcumin, carbobenzoxy-Leu-Leu (MG132), resveratrol, garlic organosulfur compounds, allicin, 4-hydroxynonenal (4-HNE), α-lipoic acid, hydrogen sulfate, and 17α-estradiol have been used as therapeutic targets to reduce cardiac remodeling, but prodrugs of monomethyl fumarate have not been used yet to reduce cardiac remodeling (Zhou et al; J Appl Physiol. 2015, 119(8), 944-951).

Fumarates are cardioprotective in acute situations via activation of the NRF2 pathway in acute ischemia due to myocardial infarction (Ashrafian et. al; Cell Metab. 2012, 15(3), 361-71). However, Ashrafian et. al claims that fumarates are harmful in chronic situations, including heart failure. Prodrugs of methyl hydrogen fumarate are herein proposed to achieve the intended effect, for example, treatment of chronic heart failure with preserved ejection fraction (HFPEF).

Dimethyl Fumarate has been tested for multiple sclerosis and psoriasis at multiple dosages in the past, including 120 mg, 240 mg, daily, BID, and TID. The side effect profile was similar regardless of which dosage was used. In order to determine dosage of a prodrug of monomethyl fumarate, a dose escalation study may be conducted to find a comparable dosage of the MHF prodrug to DMF's 240 mg dose, by comparing plasma levels of MMF. For example, one MHF prodrug known as XP23829, (N,N-diethylcarbamoyl)methyl methyl (2E)but-2-ene-1,4-dioate has been tested in such a way to determine that 400 mg of XP23829 is a comparable dose of 240 mg DMF (Tecfidera) by comparing plasma levels of MHF. (Phase1 data XP23829: Steady state pharmacokinetics of formulations of XP23829, a novel prodrug of monomethyl fumarate (MMF), in healthy subjects 66th Annu Meet Am Acad Neurol (AAN) (April 26-May 3, Philadelphia) 2014, Abst P1.188, Neurology Apr. 8, 2014 vol. 82 no. 10 Supplement P1.188). Various dosages of an MHF prodrug will be tested in HFPEF subjects so that the dosage that is comparable to a DMF dosage of 120 mg, 240 mg, daily, BID, and TID may be determined. Using XP23829 as one such MHF, such dosage is calculated to be 200 mg, 400 mg, daily, BID, TID in subjects with HFPEF.

Furthermore, pro-inflammatory cytokines IL-6 and TNF-α are raised in HFPEF, which may lead to increase activity of VCAM, E-Selection, and NADPH oxidase, which increase ROS in coronary microvasculature endothelial cells, leading to the hallmarks of HFPEF: ventricular stiffness, impaired relaxation, and cardiac dysfunction. The prodrugs of methyl hydrogen fumarate may reduce damage of ROS in heart failure by multiple pathways including increasing the NRF2/ARE pathway, and possibly by reducing NF-kB, which reduces IL-6 and TNF-α.

LCZ696, a combined angiotensin receptor neprilysin inhibitor (ARNI) that has recently shown to reduce mortality in HFREF but not in HFPEF subjects. LCZ696 inhibits natriuretic peptide breakdown and enhances cGMP activation, and in HFPEF was associated with incremental reductions in circulating N-terminal pro-B-type natriuretic peptide (NT-proBNP) levels when compared to treatment with the ARB valsartan, alone. However, these reductions were incremental, and it is yet to be seen whether LCZ696 or other angiotensin receptor-neprilysin inhibitors will lead to any significant mortality or clinical benefit in HFPEF subjects. Furthermore, the comparison with ARB valsartan alone, is flawed in that ARB valsartan is used in the treatment of HFREF but not in HFPEF.

The subjects' baseline TNF-alpha, IL-6, NT-proBNP will be measured at the start of the trial and compared to levels at various intervals (weeks to months to years) to determine the ideal dosage based on reductions in TNF-alpha, IL-6, and/or NT-proBNP. Such a dosage will then be tested in a larger group of HFPEF subjects to measure changes in morbidity and mortality. Thus an ideal dosage of prodrug of MMF for treating HFPEF will be comparable to a dosage of 120 mg or 240 mg, daily, BID, or TID of DMF (Tecfidera), by measuring MMF concentrations in the blood. In the case of XP23829, this dosage range is 200 mg to 400 mg, daily, BID, or TID, for a range of 200 mg to 1200 mg during any given day.

PROPHETIC EXAMPLE 2

Based on the above prophetic example, an exemplary, non-limiting embodiment is described in detail below. As described herein, a user may include a male or female between the ages of 50 to 100 with ejection fraction of greater than 40%, and more likely to be a female with a documented history of high blood pressure, diabetes, and/or COPD, with at least one episode of fluid overload, or who has HFPEF or is at risk of developing (HFPEF).

The most common disease leading to HFPEF is systolic hypertension, which is present in more than 85% of subjects. Subjects with HFPEF have normal left ventricular (LV) end-diastolic volume and normal (or near-normal) EF and stroke volume and commonly exhibit concentric remodeling of either the LV chamber and/or cardiomyocytes.

Subjects with HFPEF have a devastating 5-year mortality rate (approaching 60%), costly morbidity (6-month hospitalization rate of 50%), and debilitating symptoms (maximum myocardial oxygen consumption [MVo$_2$] averaging 14 mL/g/min).

More than half of heart failure subjects have heart failure with preserved ejection fraction (HFPEF). Morbidity and mortality of HFPEF are similar to HFREF; however, medications proven effective in HFREF have not been found to be effective in HFPEF. At present there are no approved treatments to reduce mortality in HFPEF. In HFREF, medications such as beta-blockers, ace-inhibitors, angiotensin receptor blockers, isosorbide dinitrate, hydralazine, aldosterone inhibitors, and angiotensin receptor neprilysin inhibitors have been shown to provide benefit. However, these medications have not shown to be beneficial in subjects with HFPEF, and are not approved therapies for HFPEF.

PROPHETIC EXAMPLE 3

The following prophetic example serves to provide a combination therapy for subjects with HFPEF, which includes a prodrug of MHF with a statin. To date there has been no prospective studies of statins in subjects with HFPEF. However, statins have pleotropic effects, in which they have been shown to be beneficial to non-HFPEF subjects beyond what was predicted based on their ability to reduce cholesterol, likely through anti-inflammatory pathways. By combining a statin with a prodrug of MHF, a synergistic effect to reduce the ROS associated with HFPEF is expected, which in turn will reduce stiffness in HFPEF and also reduce biomarkers such as IL-6, TNF-alpha, or NT-proBNP, and ultimately improve survival in HFPEF subjects. In one such example, a dose range between 200 mg to 1200 mg of MHF (XP23829) will be given to a subject with a statin dosage between 10 mg to 80 mg.

As used in the description and claims, the singular form "a", "an" and "the" include both singular and plural references unless the context clearly dictates otherwise. For example, the term "prodrug" may include, and is contemplated to include, a plurality of prodrugs. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a method, substance, or composition.

As used herein, the term "comprising" or "comprises" is intended to mean that the methods and compositions include the recited elements, and may additionally include any other elements. "Consisting essentially of" shall mean that the methods and compositions include the recited elements and exclude other elements of essential significance to the combination for the stated purpose. Thus, a method or composition consisting essentially of the elements as defined herein would not exclude other materials, features, or steps that do not materially affect the basic and novel characteristic(s) of the claimed disclosure. "Consisting of" shall mean that the methods and compositions include the recited elements and exclude anything more than a trivial or inconsequential element or step. Embodiments defined by each of these transitional terms are within the scope of this disclosure.

The terms "optionally" as used herein means that a subsequently described event or circumstance may but need not occur, and that the description includes instances where the event or circumstance occurs and instances in which it does not.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed:

1. A method of treating heart failure with preserved ejection fraction in a subject having heart failure with preserved ejection fraction, wherein treating consists of reducing mortality or improving survival, the method comprising administering to the subject in need thereof a therapeutically effective amount of a compound of Formula (I) or a pharmaceutically acceptable salt thereof:

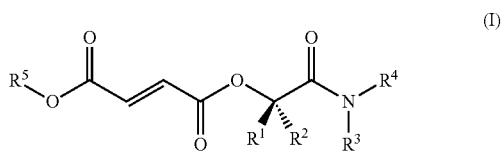

wherein:
R$^1$ and R$^2$ are independently chosen from hydrogen, C$_{1-6}$ alkyl, and substituted C$_{1-6}$ alkyl;

R³ and R⁴ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or R³ and R⁴ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and R⁵ is methyl;

wherein each substituent group is independently chosen from halogen, —OH, —CN, —CF₃, =O, —NO₂, benzyl, —C(O)NR¹¹₂, —R¹¹, —OR¹¹, —C(O)R¹¹, —COOR¹¹, and —NR¹¹ wherein each R¹¹ is independently chosen from hydrogen and $C_{1-4}$ alkyl.

2. The method of claim 1, wherein the compound is (N,N-diethylcarbamoyl)methyl methyl (2E)but-2-ene-1,4-dioate or a pharmaceutically acceptable salt thereof.

3. The method of claim 1, wherein a pharmaceutical composition is administered to the subject, wherein said pharmaceutical composition comprises a therapeutically effective amount of (N,N-diethylcarbamoyl)methyl methyl (2E)but-2-ene-1,4-dioate or a pharmaceutically acceptable salt thereof that is shown to provide an MMF plasma concentration proportional to administered dimethyl fumarate at 120 mg to 720 mg per day.

4. The method of claim 1, wherein a pharmaceutical composition is administered to the subject, wherein said pharmaceutical composition comprises about 200 mg to 1200 mg of (N,N-diethylcarbamoyl)methyl methyl (2E)but-2-ene-1,4-dioate or a pharmaceutically acceptable salt thereof.

5. The method of claim 1, wherein (N,N-diethylcarbamoyl)methyl methyl (2E)but-2-ene-1,4-dioate or a pharmaceutically acceptable salt thereof is administered in combination with one or more second agents useful for treating heart failure with preserved ejection fraction.

6. The method of claim 5, wherein the second agent is selected from the group consisting of: a diuretic, an ACE-inhibitor, a beta-blocker, an angiotensin receptor blocker, isosorbide dinitrate, hydralazine, an angiotensin receptor-neprilysin inhibitor, an aldosterone antagonist, a PDE5 inhibitor, a statin, a neprilysin inhibitor, an aldosterone inhibitor, and an antitumor necrosis factor-alpha therapy.

7. The method of claim 6, wherein the second agent is the statin.

8. A method of treating heart failure with preserved ejection fraction in a subject having heart failure with preserved ejection fraction, wherein treating consists of reducing mortality or improving survival, the method comprising: administering to the subject a therapeutically effective amount of (a) (N,N-diethylcarbamoyl)methyl methyl (2E)but-2-ene-1,4-dioate or a pharmaceutically acceptable salt thereof and either separately or together with (b) a statin.

9. The method of claim 1, wherein the heart failure with preserved ejection fraction is further characterized by elevated pro-inflammatory cytokines IL-6 and TNF-α.

10. The method of claim 8, wherein the heart failure with preserved ejection fraction is further characterized by elevated pro-inflammatory cytokines IL-6 and TNF-α.

* * * * *